United States Patent
Jung et al.

(10) Patent No.: US 12,389,793 B2
(45) Date of Patent: Aug. 12, 2025

(54) COMPOUND AND ORGANIC LIGHT EMITTING DEVICE COMPRISING THE SAME

(71) Applicant: LG CHEM, LTD., Seoul (KR)

(72) Inventors: Min Woo Jung, Daejeon (KR); Dong Hoon Lee, Daejeon (KR); Boonjae Jang, Daejeon (KR); Jungha Lee, Daejeon (KR); Su Jin Han, Daejeon (KR); Seulchan Park, Daejeon (KR); Sunghyun Hwang, Daejeon (KR)

(73) Assignee: LG CHEM, LTD., Seoul (KR)

(*) Notice: Subject to any disclaimer, the term of this patent is extended or adjusted under 35 U.S.C. 154(b) by 851 days.

(21) Appl. No.: 17/253,085

(22) PCT Filed: Jul. 8, 2019

(86) PCT No.: PCT/KR2019/008373
§ 371 (c)(1),
(2) Date: Dec. 16, 2020

(87) PCT Pub. No.: WO2020/009554
PCT Pub. Date: Jan. 9, 2020

(65) Prior Publication Data
US 2021/0280799 A1 Sep. 9, 2021

(30) Foreign Application Priority Data

Jul. 6, 2018 (KR) .................. 10-2018-0078987
Jul. 5, 2019 (KR) .................. 10-2019-0081577

(51) Int. Cl.
*H10K 85/60* (2023.01)
*C07D 209/86* (2006.01)
(Continued)

(52) U.S. Cl.
CPC ....... *H10K 85/6572* (2023.02); *C07D 209/86* (2013.01); *C07D 405/14* (2013.01);
(Continued)

(58) Field of Classification Search
CPC ............. H10K 85/6572; H10K 85/615; H10K 85/6574; H10K 85/6576; H10K 50/11;
(Continued)

(56) References Cited

U.S. PATENT DOCUMENTS

2003/0219625 A1* 11/2003 Wolk .................. H10K 85/636
427/64
2004/0251816 A1   12/2004 Leo et al.
(Continued)

FOREIGN PATENT DOCUMENTS

CN   105829279 A   8/2016
CN   111225905 A   6/2020
(Continued)

OTHER PUBLICATIONS

Im, Yirang, and Jun Yeob Lee. "Molecular design of modifying 4-position of dibenzofuran for high temperature stability and high efficiency." Dyes and Pigments 128 (2016): 84-88. (Year: 2016).*
(Continued)

*Primary Examiner* — Dawn L Garrett
(74) *Attorney, Agent, or Firm* — Bryan Cave Leighton Paisner LLP

(57) ABSTRACT

Provided is a compound of Chemical Formula 1:

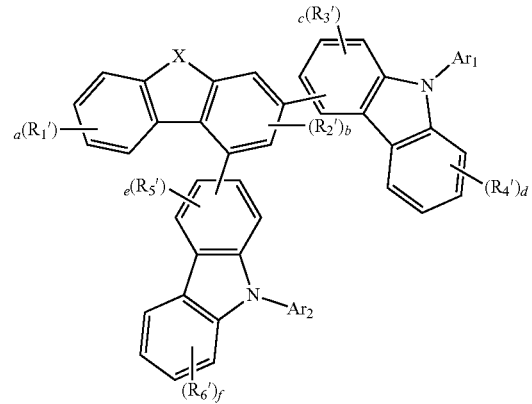

wherein, in Chemical Formula 1.

X is O, S, or $C(R_1R_2)$; $R_1$ and $R_2$ are each independently a substituted or unsubstituted $C_{1-60}$ alkyl; $Ar_1$ and $Ar_2$ are each independently a substituted or (Continued)

unsubstituted $C_{6-60}$ aryl; $R_1'$ and $R_2'$ are each independently hydrogen, deuterium, halogen, cyano, nitro, amino, or a substituted or unsubstituted $C_{1-60}$ alkyl; $R_3'$, $R_4'$, $R_5'$, and $R_6'$ are each independently hydrogen, deuterium, halogen, cyano, nitro, amino, or a substituted or unsubstituted $C_{1-60}$ alkyl; a, d, and f are each independently an integer of 0 to 4; b is an integer of 0 to 2; and c and e are each independently an integer of 0 to 3, and an organic light emitting device including the same.

9 Claims, 1 Drawing Sheet

(51) Int. Cl.
*C07D 405/14* (2006.01)
*C07D 409/14* (2006.01)
*C09K 11/06* (2006.01)
*H10K 50/11* (2023.01)
*H10K 101/10* (2023.01)

(52) U.S. Cl.
CPC .......... *C07D 409/14* (2013.01); *C09K 11/06* (2013.01); *H10K 85/615* (2023.02); *H10K 85/6574* (2023.02); *H10K 85/6576* (2023.02); *C09K 2211/1018* (2013.01); *H10K 50/11* (2023.02); *H10K 2101/10* (2023.02)

(58) Field of Classification Search
CPC .............. H10K 2101/10; C07D 209/86; C07D 405/14; C07D 409/14; C07D 209/82; C07D 307/91; C07D 333/76; C09K 11/06; C09K 2211/1018
See application file for complete search history.

(56) References Cited

U.S. PATENT DOCUMENTS

| | | | | |
|---|---|---|---|---|
| 2009/0131673 | A1* | 5/2009 | Tanabe | C07D 307/91 548/440 |
| 2012/0319094 | A1 | 12/2012 | Furukawa et al. | |
| 2013/0200340 | A1 | 8/2013 | Otsu et al. | |
| 2014/0346483 | A1 | 11/2014 | Yu et al. | |
| 2017/0186965 | A1 | 6/2017 | Parham et al. | |
| 2019/0367494 | A1* | 12/2019 | Parham | C07D 405/04 |

FOREIGN PATENT DOCUMENTS

| | | |
|---|---|---|
| JP | 2009-267255 | 11/2009 |
| JP | 2013-177361 | 9/2013 |
| KR | 10-2013-0073537 | 7/2013 |
| KR | 10-2015-0061174 | 6/2015 |
| KR | 10-2015-0066202 | 6/2015 |
| KR | 10-2015-0076129 | 7/2015 |
| KR | 10-2016-0028524 | 3/2016 |
| KR | 10-2017-0053590 | 5/2017 |
| KR | 10-2017-0116692 A | 10/2017 |
| KR | 10-2017-0116992 | 10/2017 |
| WO | 2003-012890 | 2/2003 |
| WO | 2006-132139 | 12/2006 |
| WO | 2011-102249 | 8/2011 |
| WO | 2013-168534 | 11/2013 |
| WO | 2015-041492 | 3/2015 |
| WO | 2015-084114 | 6/2015 |
| WO | 2015-099485 | 7/2015 |
| WO | 2017-078494 | 5/2017 |
| WO | 2017-179911 | 10/2017 |

OTHER PUBLICATIONS

Jeong, Sook Hee, and Jun Yeob Lee. "Dibenzothiophene derivatives as host materials for high efficiency in deep blue phosphorescent organic light emitting diodes." Journal of Materials Chemistry 21.38 (2011): 14604-14609. (Year: 2011).*

Lin, Wei-Chieh, et al. "A bipolar host containing carbazole/dibenzothiophene for efficient solution-processed blue and white phosphorescent OLEDs." Journal of Materials Chemistry C 1.41 (2013): 6835-6841. (Year: 2013).*

* cited by examiner

[FIG. 1]
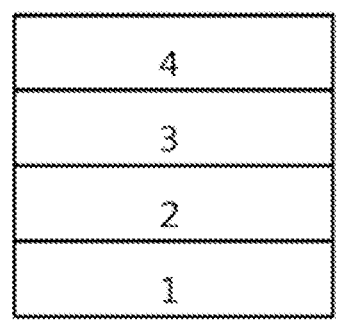
[FIG. 2]
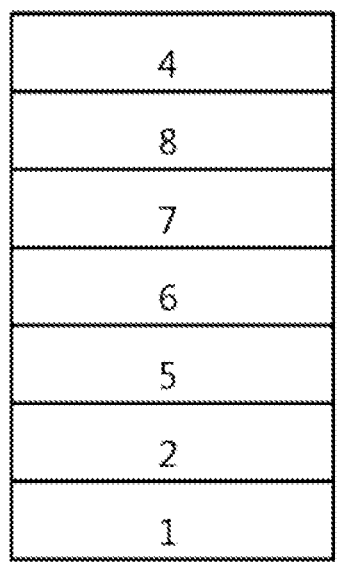

COMPOUND AND ORGANIC LIGHT EMITTING DEVICE COMPRISING THE SAME

CROSS-REFERENCE TO RELATED APPLICATIONS

This application is a National Stage Application of International Application PCT/KR2019/008373 filed on Jul. 8, 2019, which claims priority to and the benefit of Korean Patent Application No. 10-2018-0078987 filed with the Korean Intellectual Property Office on Jul. 6, 2018 and Korean Patent Application No. 10-2019-0081577 filed with the Korean Intellectual Property Office on Jul. 5, 2019, the disclosures of which are incorporated herein by reference in their entirety.

TECHNICAL FIELD

The present invention relates to a novel compound and to an organic light emitting device comprising the same.

BACKGROUND

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently has a multilayered structure that comprises different materials in order to enhance efficiency and stability of the organic light emitting device, and for example, the organic material layer can be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and electrons meet each other, an exciton is formed, and light is emitted when the exciton falls to a ground state again.

There is a continuing need for the development of new materials for the organic materials used in the organic light emitting devices as described above.

PRIOR ART LITERATURE

Patent Literature (Patent Literature 0001) Korean Unexamined Patent Publication No. 10-2013-073537

BRIEF DESCRIPTION

Technical Problem

It is an object of the present invention to provide a novel compound and an organic light emitting device including the same.

Technical Solution

In one aspect of the invention, there is provided a compound of the following Chemical Formula 1;

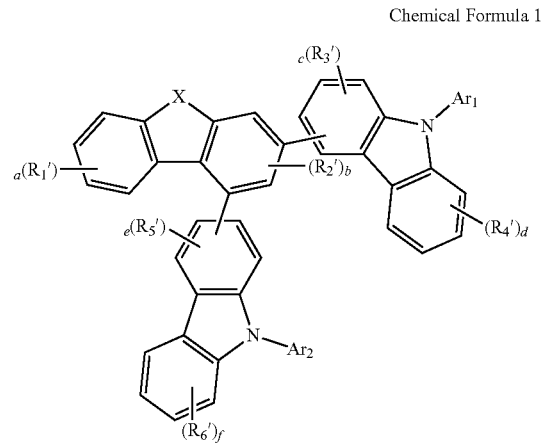

Chemical Formula 1 wherein, in Chemical Formula 1:
X is O, S, or $C(R_1R_2)$;
$R_1$ and $R_2$ are each independently a substituted or unsubstituted $C_{1-60}$ alkyl;
$Ar_1$ and $Ar_2$ are each independently a substituted or unsubstituted $C_{6-60}$ aryl;
$R_1'$ and $R_2'$ are each independently hydrogen, deuterium, halogen, cyano, nitro, amino, or a substituted or unsubstituted $C_{1-60}$ alkyl;
$R_3'$, $R_4'$, $R_5'$ and $R_6'$ are each independently hydrogen, deuterium, halogen, cyano, nitro, amino, or a substituted or unsubstituted $C_{1-60}$ alkyl;
a, d, and f are each independently an integer of 0 to 4;
b is an integer of 0 to 2; and
c and e are each independently an integer of 0 to 3.

In another aspect of the prevent invention, there is provided an organic light emitting device including a first electrode; a second electrode that is disposed opposite to the first electrode; and one or more organic material layers that are disposed between the first electrode and the second electrode, wherein one or more layers of the organic material layers include the compound of the present invention described above.

Advantageous Effects

The compound of Chemical Formula 1 described above can be used as a material of an organic material layer of an organic light emitting device, and can improve achieve low driving voltage and/or the efficiency, improve lifetime characteristics in the organic light emitting device. In particular, the compound of Chemical Formula 1 can be used as a hole injection material, hole transport material, hole injection and transport material, light emitting material, electron transport material, or electron injection material.

BRIEF DESCRIPTION OF THE DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8 and a cathode 4.

DETAILED DESCRIPTION

Hereinafter, embodiments of the present invention will be described in more detail to facilitate understanding of the invention.

The present invention provides a compound of the following Chemical Formula 1:

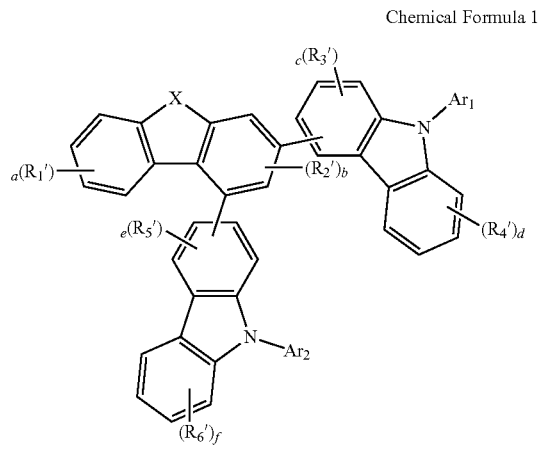

Chemical Formula 1 wherein, in Chemical Formula 1:

X is O, S, or C($R_1R_2$);

$R_1$ and $R_2$ are each independently a substituted or unsubstituted $C_{1-60}$ alkyl;

$Ar_1$ and $Ar_2$ are each independently a substituted or unsubstituted $C_{6-60}$ aryl;

$R_1'$ and $R_2'$ are each independently hydrogen, deuterium, halogen, cyano, nitro, amino, or a substituted or unsubstituted $C_{1-60}$ alkyl;

$R_3'$, $R_4'$, $R_5'$, and $R_6'$ are each independently hydrogen, deuterium, halogen, cyano, nitro, amino, or a substituted or unsubstituted $C_{1-60}$ alkyl;

a, d, and f are each independently an integer of 0 to 4;

b is an integer of 0 to 2; and c and e are each independently an integer of 0 to 3.

As used herein, the notation $\xi$ means a bond linked to another substituent group.

As used herein, the term "substituted or unsubstituted" means being unsubstituted or substituted with one or more substituents selected from the group consisting of deuterium, halogen group, a nitrile group, a nitro group, a hydroxy group, a carbonyl group, an ester group, an imide group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, an aralkylamine group, a heteroarylamine group, an arylamine group, an arylphosphine group, and a heterocyclic group containing at least one of N, O and S atoms, or being unsubstituted or substituted with a substituent to which two or more substituents are linked among the substituents exemplified above. For example, "the substituent to which two or more substituents are linked" can be a biphenyl group. That is, the biphenyl group can also be an aryl group and can be interpreted as a substituent to which two phenyl groups are linked.

In the present specification, the number of carbon atoms of a carbonyl group is not particularly limited, but is preferably 1 to 40. Specifically, the carbonyl group can be a compound having the following structural formulas, but is not limited thereto:

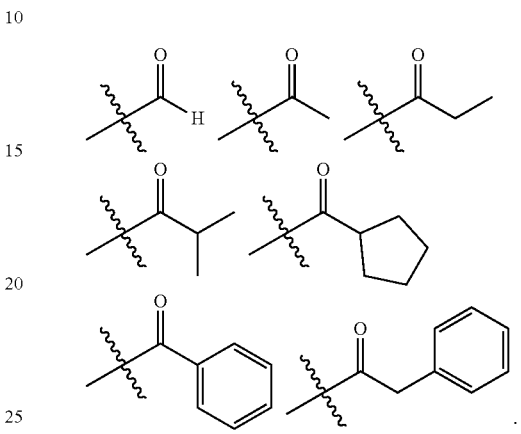

In the present specification, an ester group can have a structure in which oxygen of the ester group can be substituted by a straight-chain, branched-chain, or cyclic alkyl group having 1 to 25 carbon atoms, or an aryl group having 6 to 25 carbon atoms. Specifically, the ester group can be a compound having the following structural formulas, but is not limited thereto:

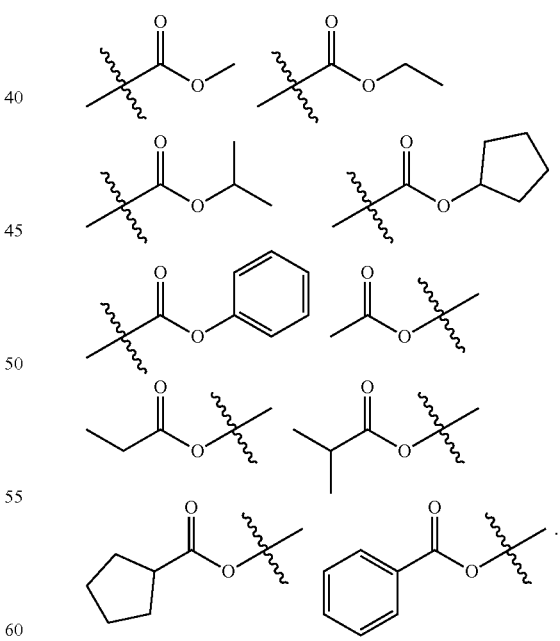

In the present specification, the number of carbon atoms of an imide group is not particularly limited, but is preferably 1 to 25. Specifically, the imide group can be a compound having the following structural formulas, but is not limited thereto:

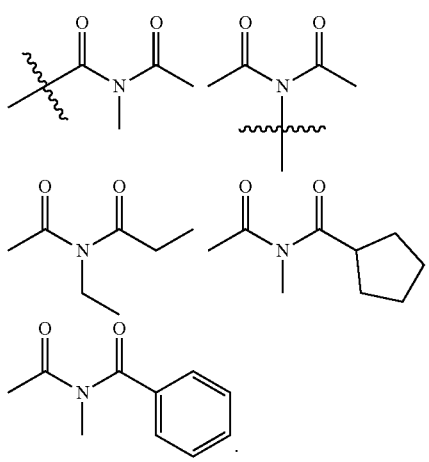

In the present specification, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but is not limited thereto.

In the present specification, a boron group specifically includes a trimethylboron group, a triethylboron group, a t-butyldimethylboron group, a triphenylboron group, and a phenylboron group, but is not limited thereto.

In the present specification, examples of a halogen group fluorine, chlorine, bromine, or iodine.

In the present specification, the alkyl group can be straight-chain or branched-chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to another embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentyl-methyl, cyclohexyl-methyl, octyl, n-octyl, tert-octyl, 1-methylheptyl, 2-ethylhexyl, 2-propylpentyl, n-nonyl, 2,2-dimethyl-heptyl, 1-ethyl-propyl, 1,1-dimethyl-propyl, iso-hexyl, 2-methylpentyl, 4-methylhexyl, 5-methylhexyl, and the like, but are not limited thereto.

In the present specification, the alkenyl group can be straight-chain or branched-chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenyl-vinyl-1-yl, 2-phenyl-2-(naphthyl-1-yl) vinyl-1-yl, 2,2-bis(diphenyl-1-yl) vinyl-1-yl, a stilbenyl group, a styrenyl group, and the like, but are not limited thereto.

In the present specification, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6.

Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, an aryl group is not particularly limited, but preferably has 6 to 60 carbon atoms, and it can be a monocyclic aryl group or a polycyclic aryl group. According to one embodiment, the number of carbon atoms of the aryl group is 6 to 30.

According to one embodiment, the number of carbon atoms of the aryl group is 6 to 20. The aryl group can be a phenyl group, a biphenyl group, a terphenyl group or the like as the monocyclic aryl group, but is not limited thereto. The polycyclic aryl group includes a naphthyl group, an anthracenyl group, a phenanthryl group, a pyrenyl group, a perylenyl group, a chrysenyl group, a fluorenyl group or the like, but is not limited thereto.

In the present specification, a fluorenyl group can be substituted, and two substituent groups can be bonded to each other to form a spiro structure. In the case where the fluorenyl group is substituted,

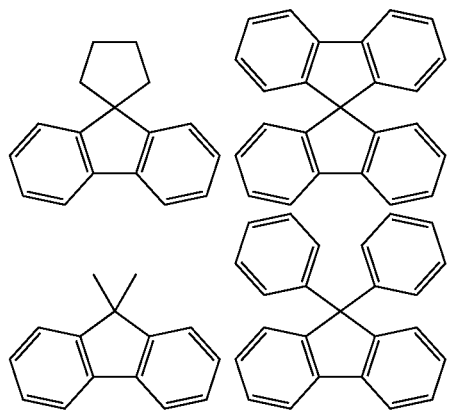

and the like can be formed. However, the structure is not limited thereto.

In the present specification, a heterocyclic group is a heterocyclic group including one or more of O, N, Si and S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzo-thiazol group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group in the aralkyl group, the aralkenyl group, the alkylaryl group and the arylamine group is the same as the aforementioned examples of the aryl group. In the present specification, the alkyl group in the aralkyl group, the alkylaryl group and the alkylamine group is the same as the aforementioned examples of the alkyl group. In the present specification, the heteroaryl in the heteroarylamine can be applied to the aforementioned description of the heterocyclic group. In the present specification, the alkenyl group in the aralkenyl group is the same as the aforementioned examples of the alkenyl group. In the present specification, the aforementioned description of the aryl group can be applied except that the arylene is a divalent group. In the present specification, the aforementioned description of the heterocyclic group can be applied except that the heteroarylene is a divalent group. In the present specification, the aforementioned description of the aryl group or cycloalkyl group can be applied except that the hydrocarbon ring is not a monovalent group but formed by combining two substituent groups. In the present specification, the aforementioned description of the heterocyclic group can be applied, except that the heterocyclic group is not a monovalent group but formed by combining two substituent groups.

Preferably, $R_1$ and $R_2$ are each independently methyl, ethyl or propyl.

Preferably. $Ar_1$ and $Ar_2$ are each independently any one selected from the group consisting of the following:

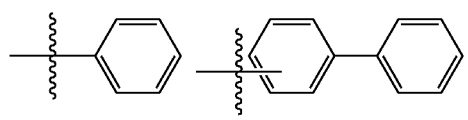

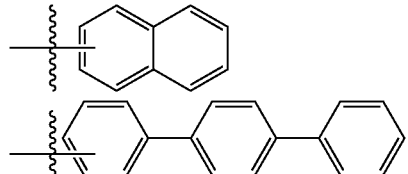

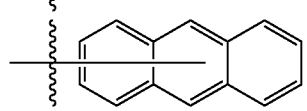

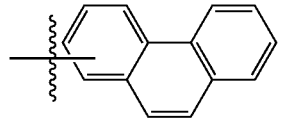

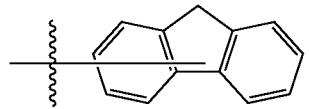

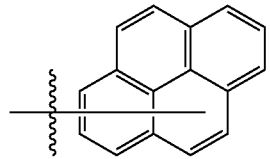

Preferably, $Ar_1$ and $Ar_2$ are each independently

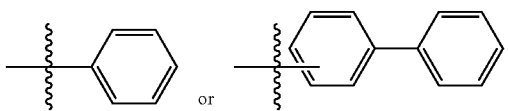

Preferably, $R_1'$ and $R_2'$ are each independently hydrogen.

Preferably, $R_3'$, $R_4'$, $R_5'$, and $R_6'$ are each independently hydrogen.

Preferably, the compound of Chemical Formula 1 is any one compound selected from the group consisting of the following compounds:

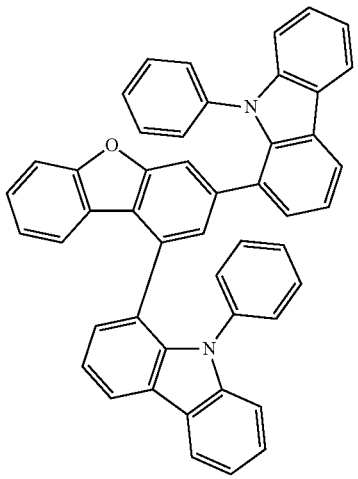

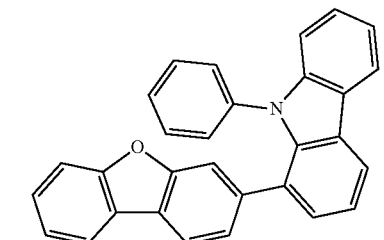

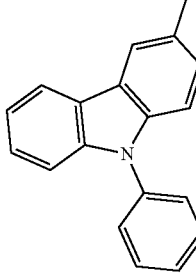

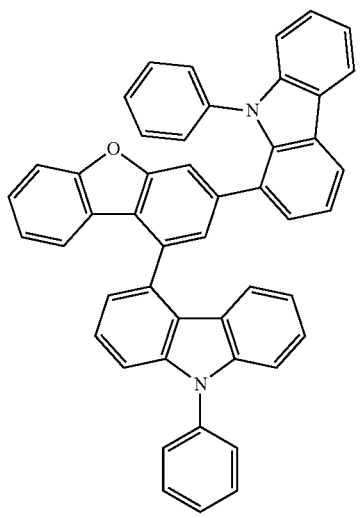
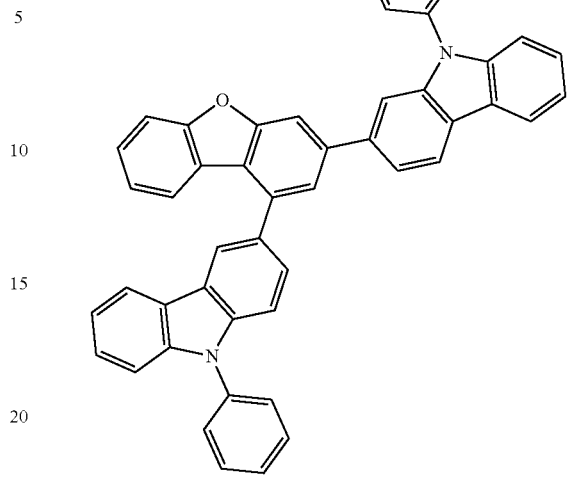
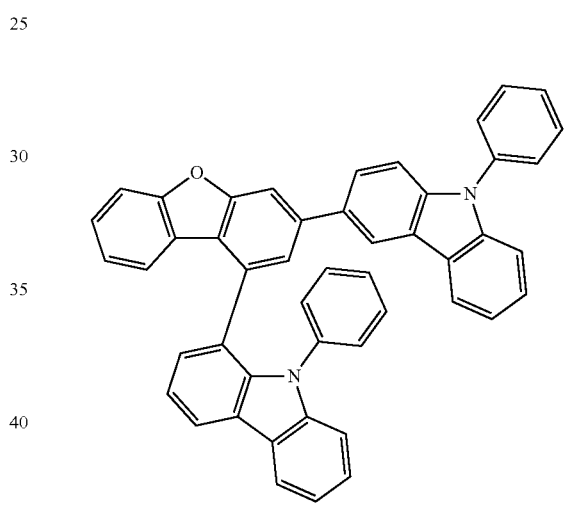
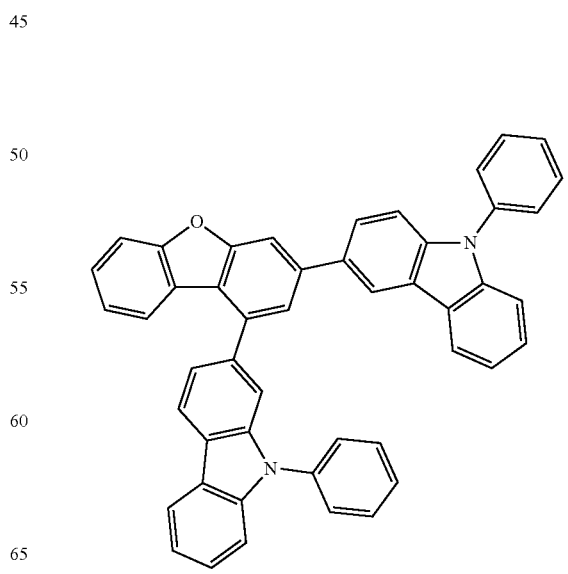

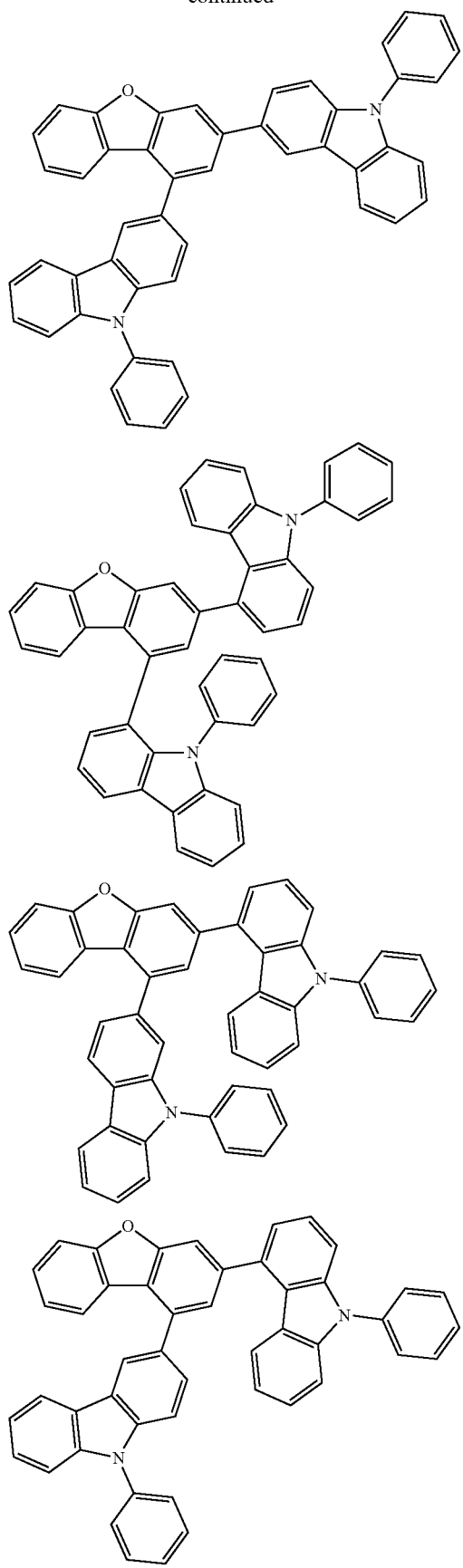
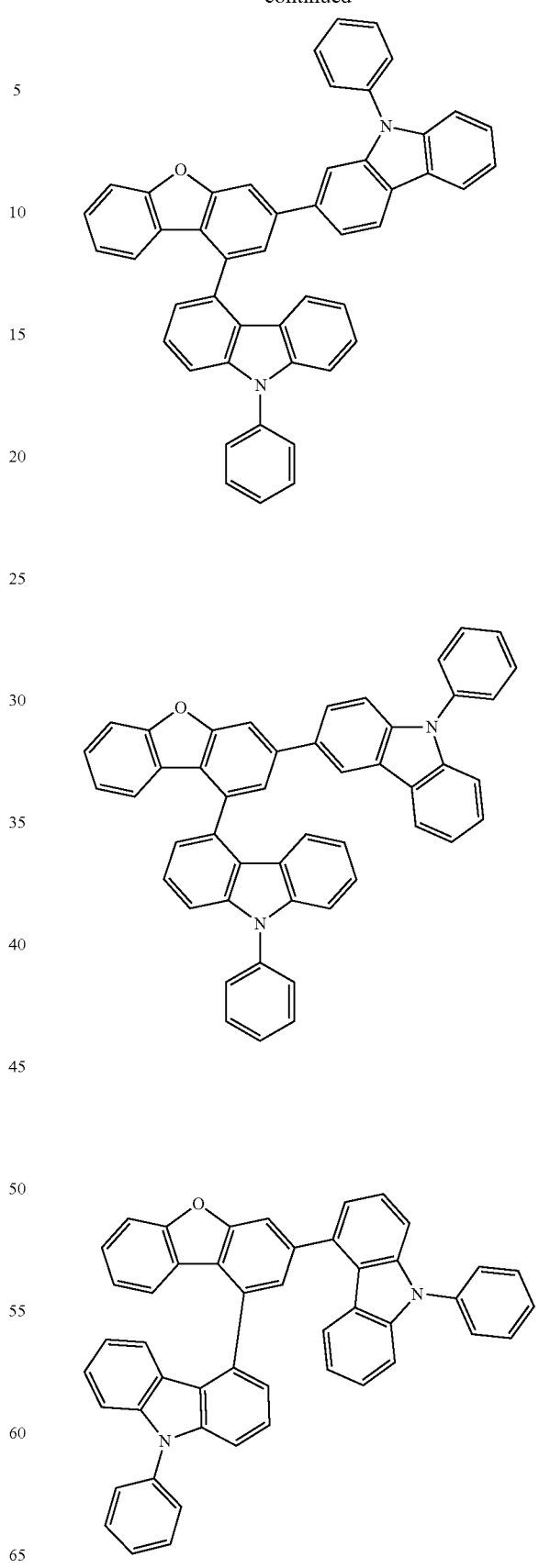

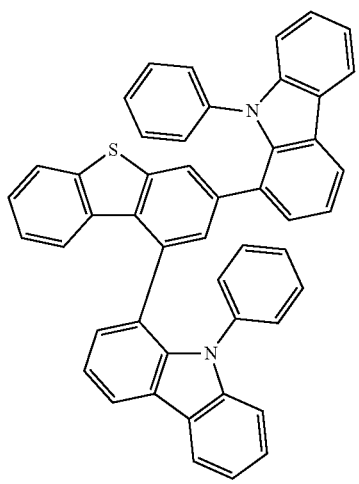
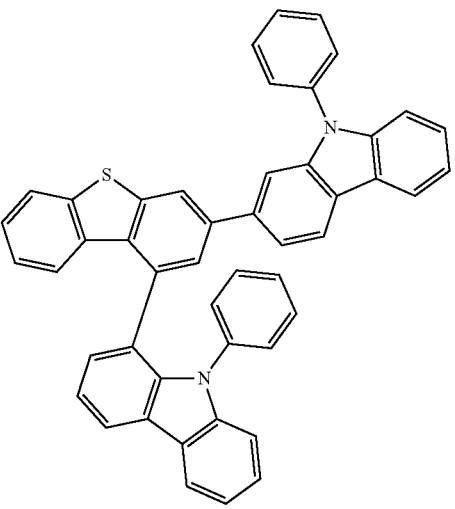
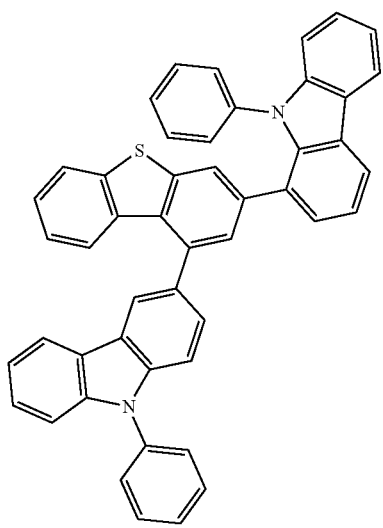
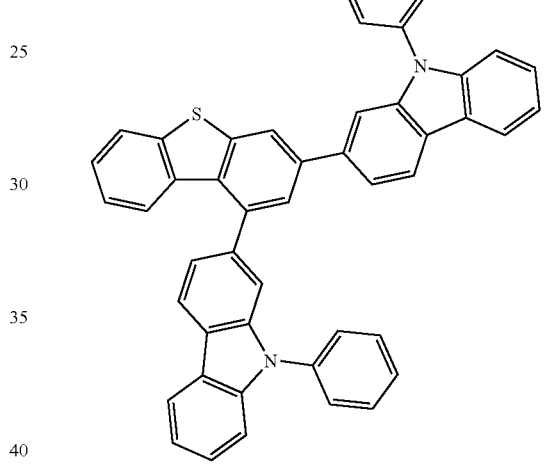
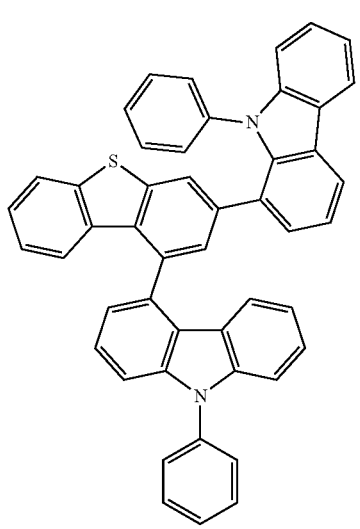
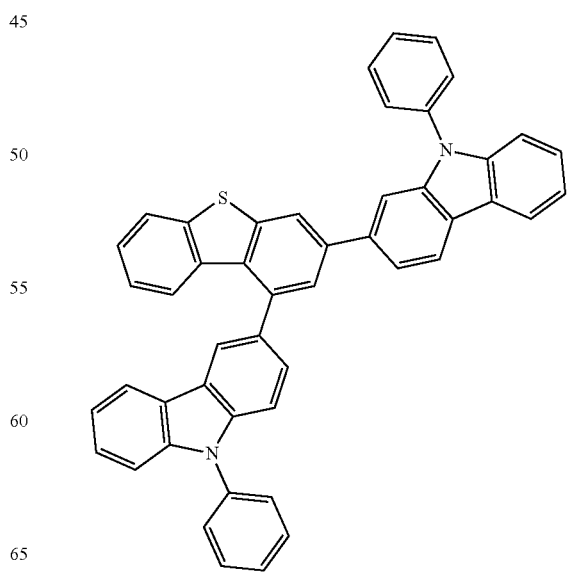

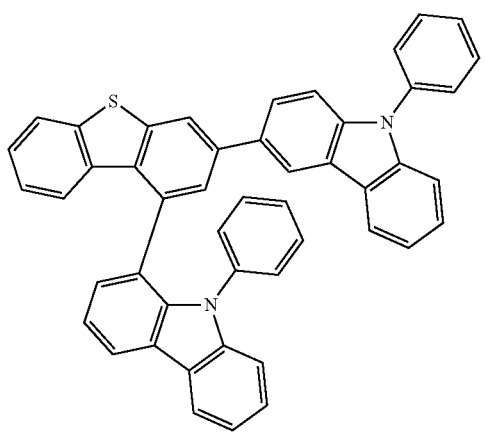
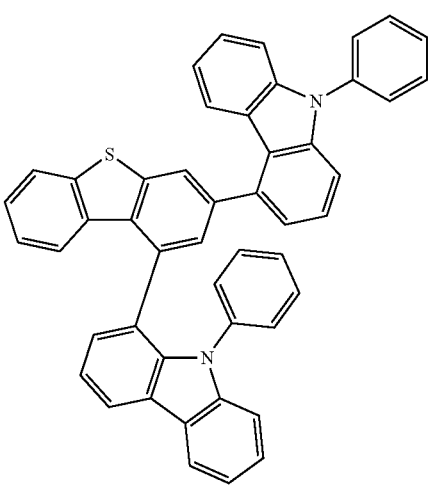
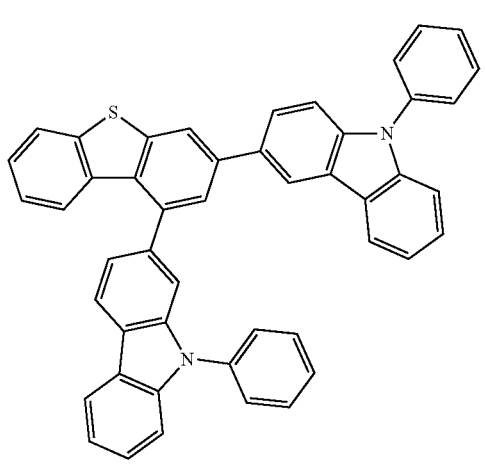
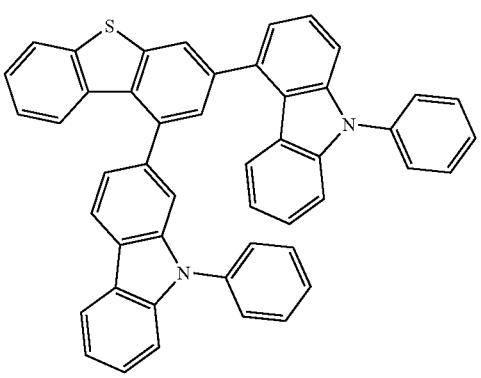
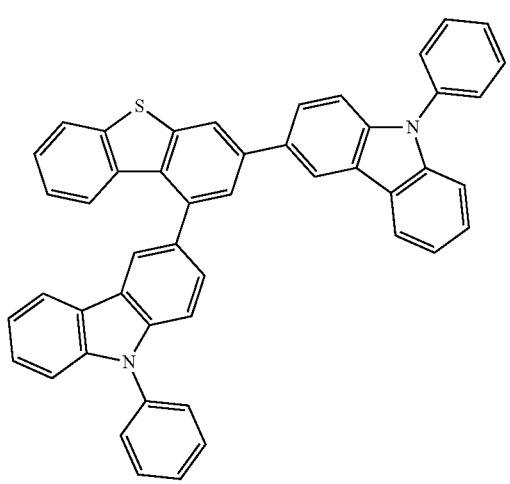
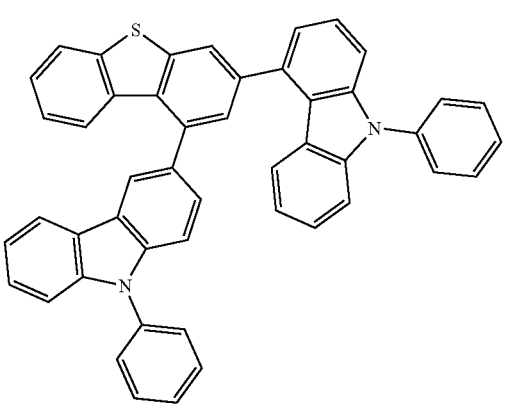

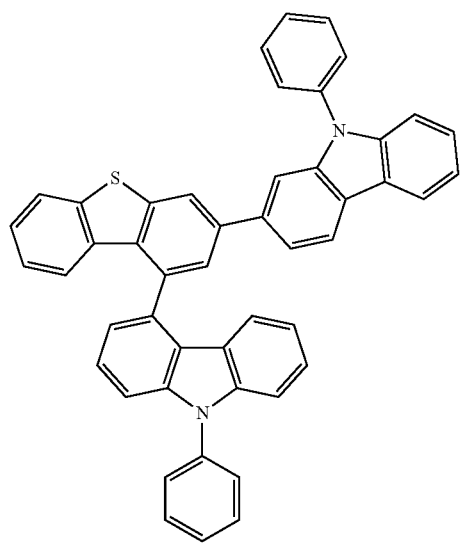
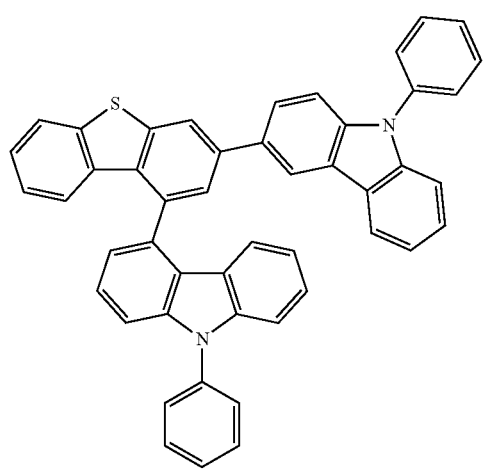
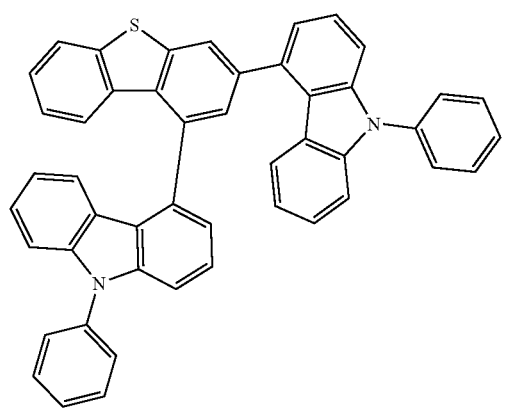
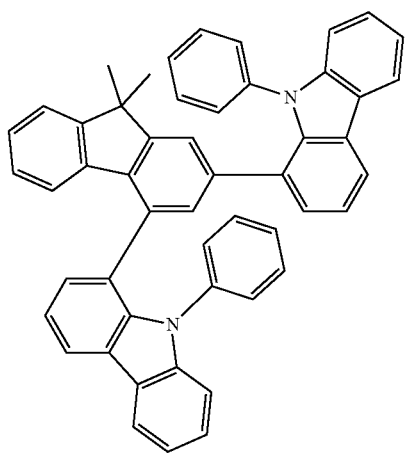
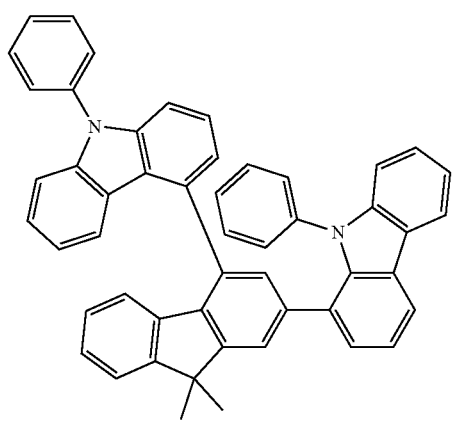
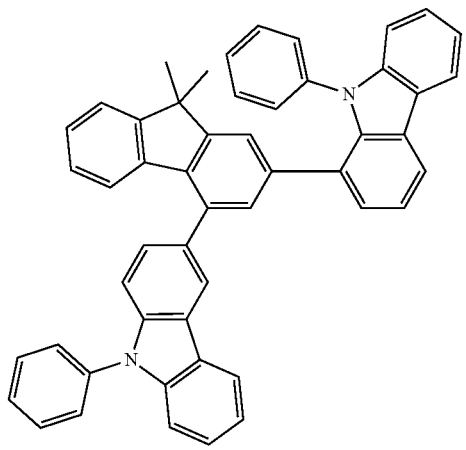

-continued
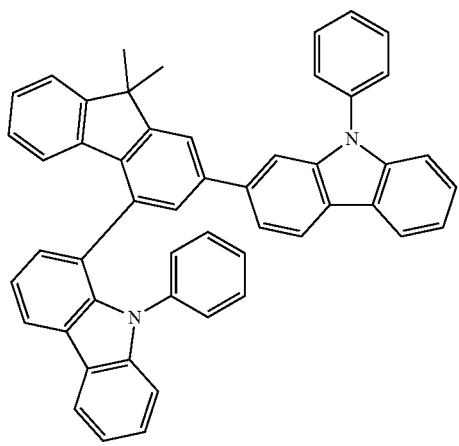
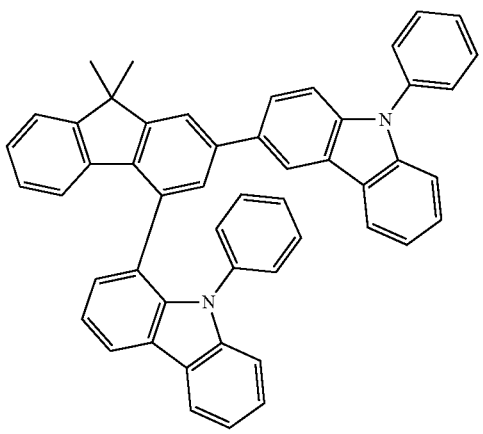
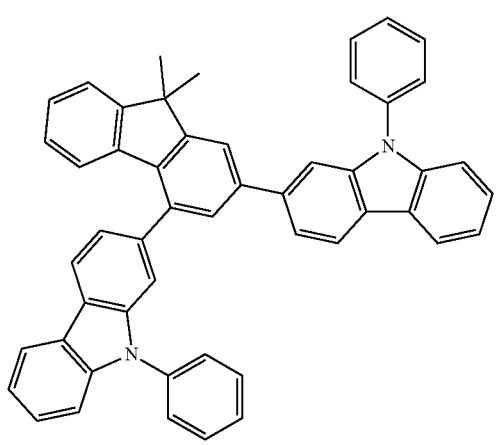
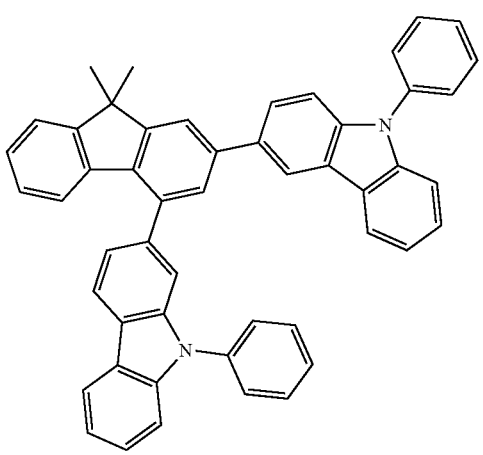
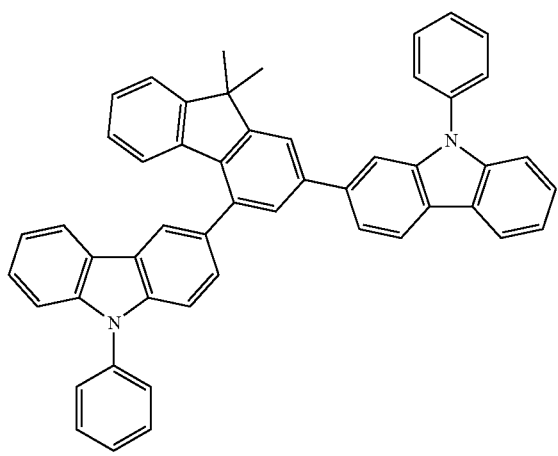
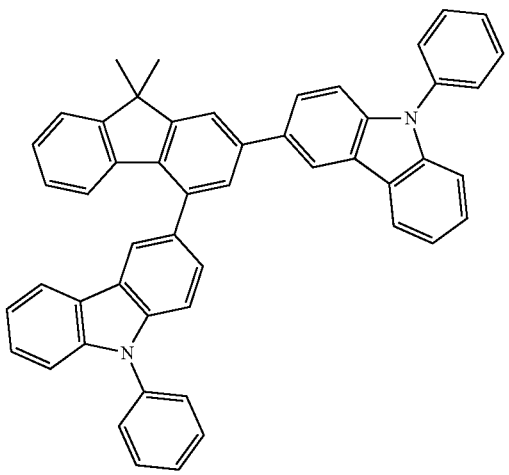

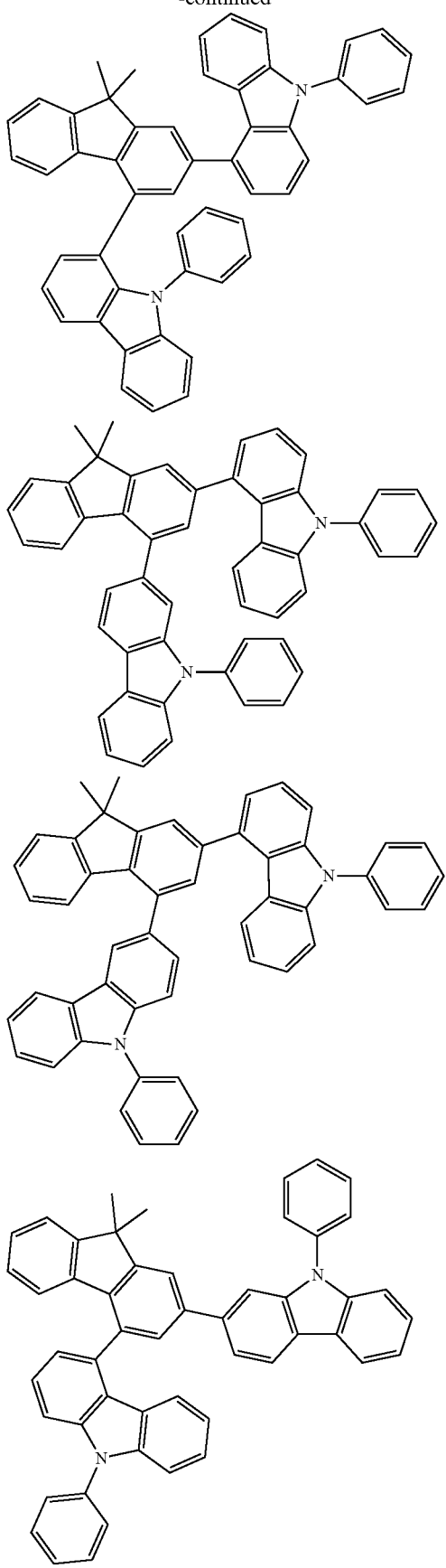
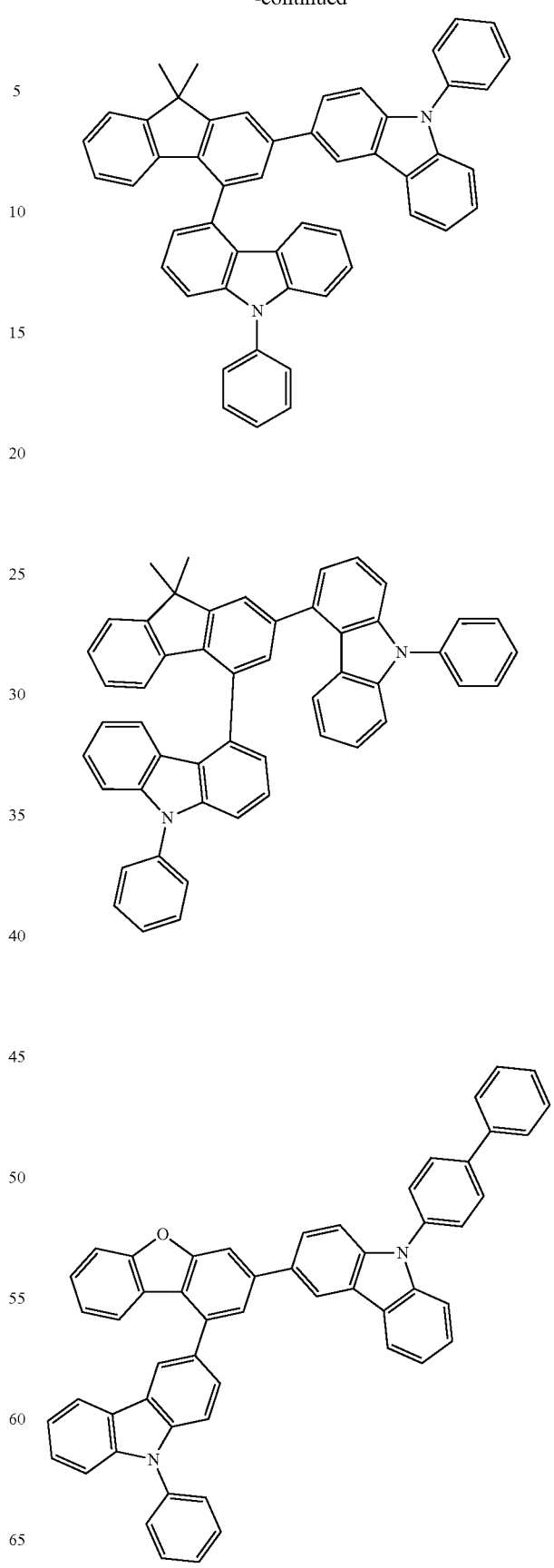

23
-continued
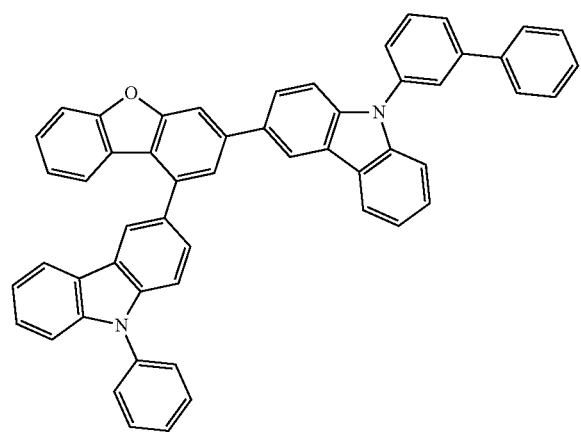
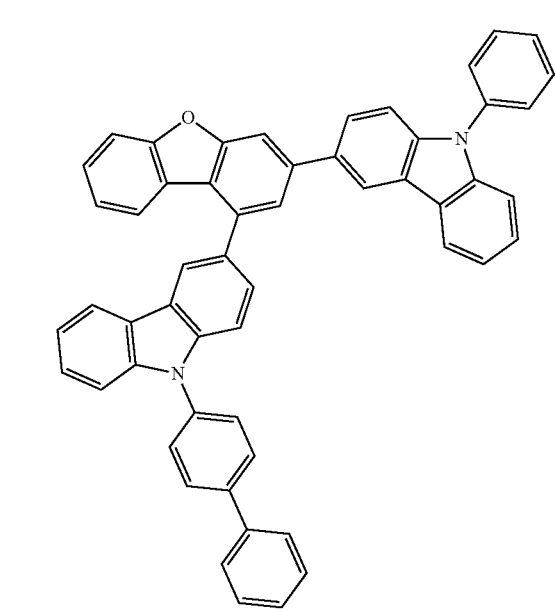
24
-continued
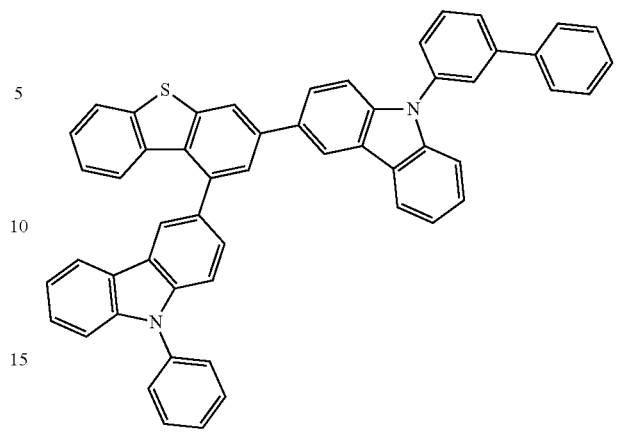
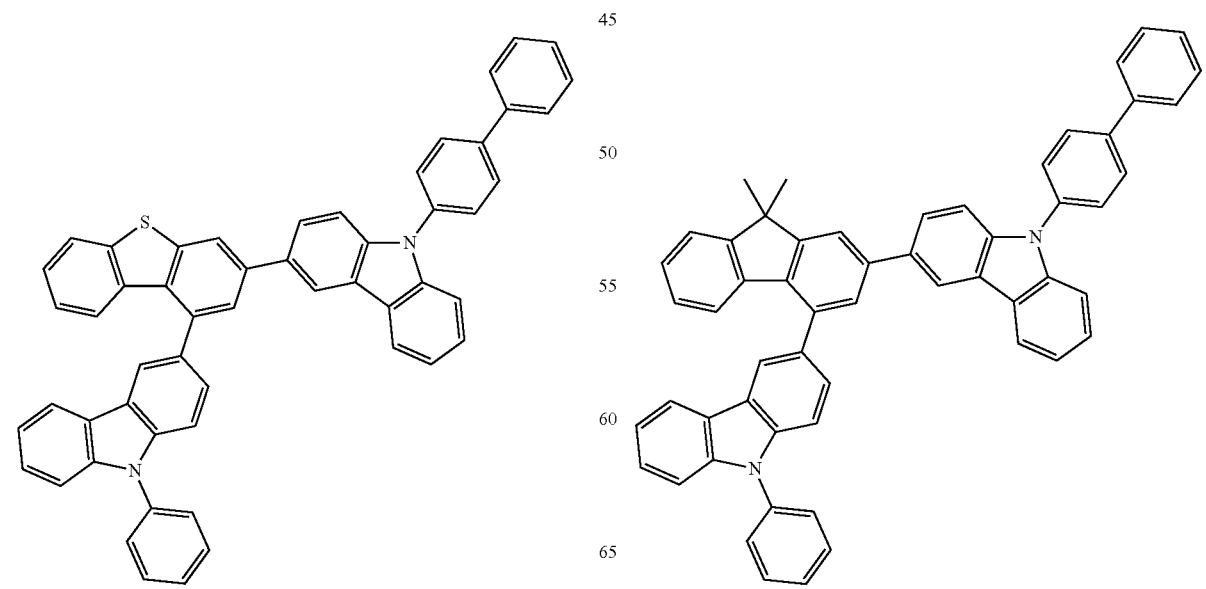

-continued

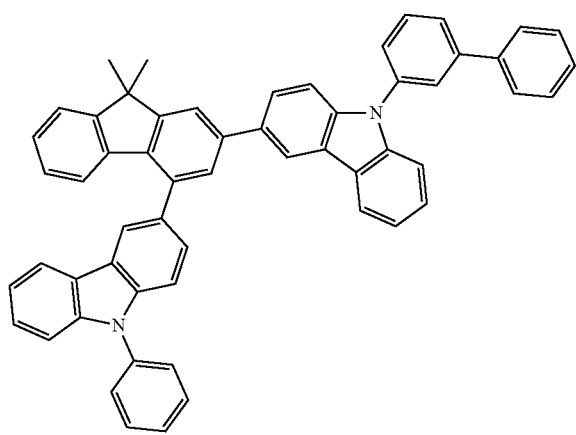

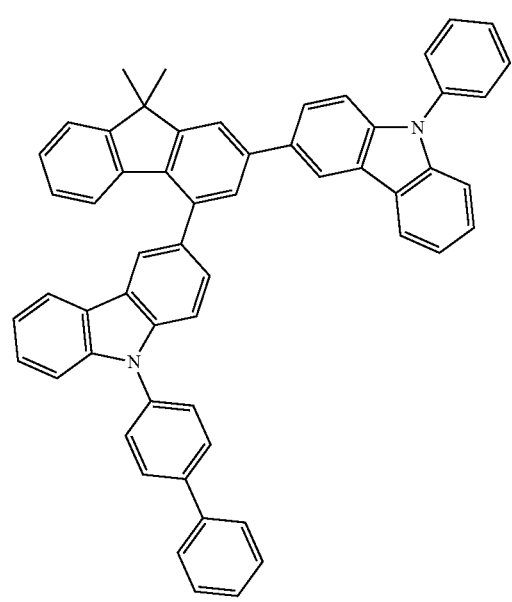

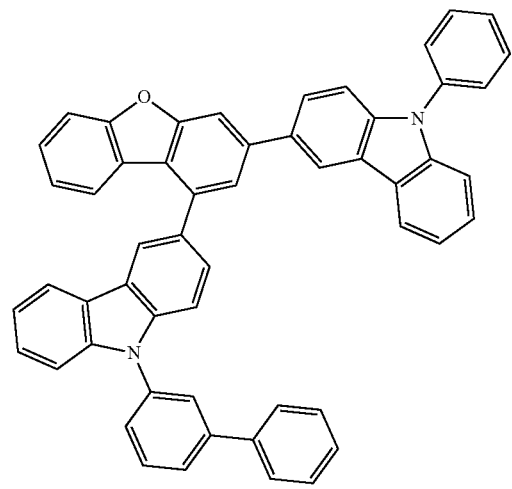

-continued

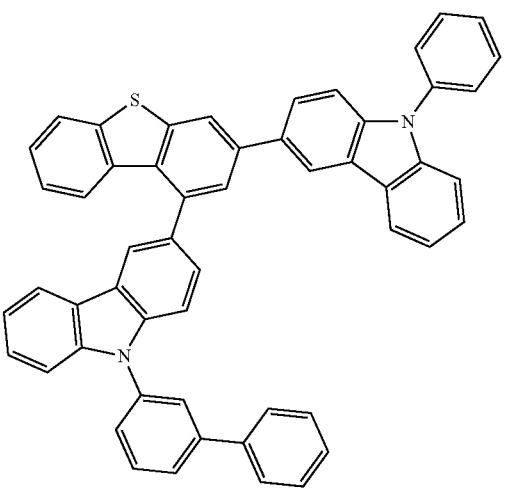

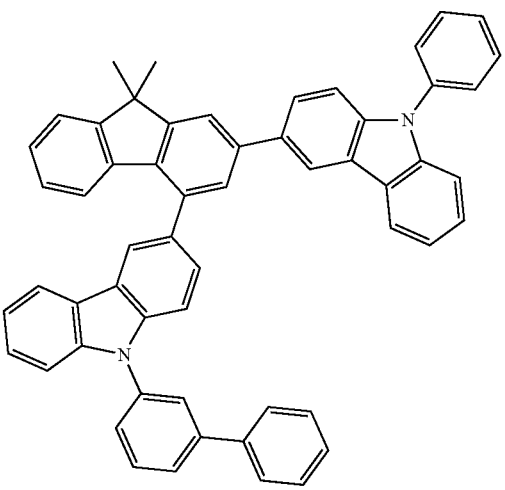

The compound of Chemical Formula 1 according to the present invention has a core structure of dibenzofuran (dibenzothiophene, dialkylfluorene). Due to their structural characteristics including carbazoles at positions 1 and 3, the electron and hole stability are significantly improved. Accordingly, when applied to the organic light emitting device, it can have high efficiency, low driving voltage, high luminance, and long lifetime.

The compound of Chemical Formula 1 can be prepared through the following Reaction Scheme 1.

Reaction Scheme 1

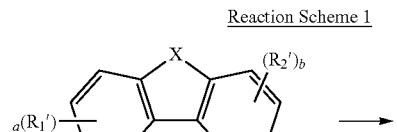

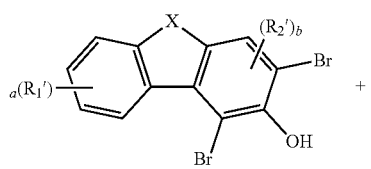

-continued

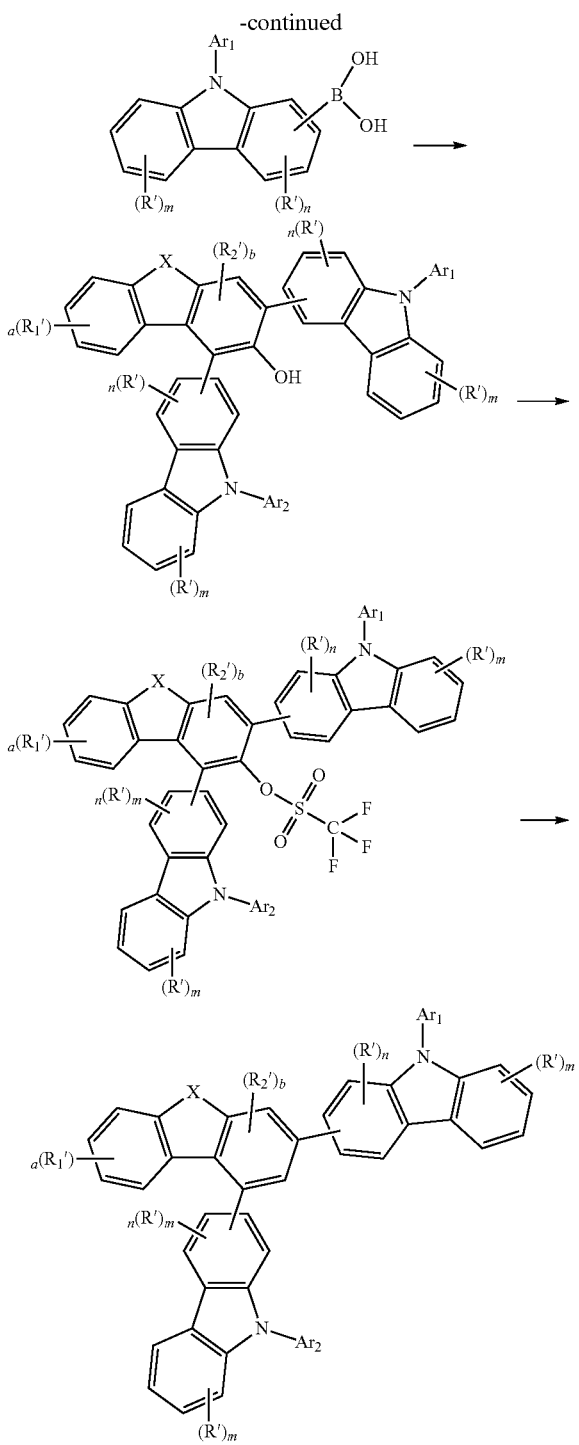

In Reaction Scheme 1, X, Ar$_1$, Ar$_2$, R$_1$', R$_2$', a and b are the same as defined in Chemical Formula 1. Each R' is independently hydrogen, deuterium, halogen, cyano, nitro, amino, or a substituted or unsubstituted C$_{1-60}$ alkyl; n is an integer of 0 to 3; and m is an integer of 0 to 4. In the above Reaction Scheme, the types of reactants, catalysts and the like used can be appropriately selected. The preparation method can be more embodied in the Preparation Examples described hereinafter.

In another embodiment of the invention, there is provided an organic light emitting device including a compound of Chemical Formula 1 described above. As an example, there is provided an organic light emitting device including a first electrode; a second electrode that is disposed opposite to the first electrode; and one or more organic material layers that are disposed between the first electrode and the second electrode, wherein one or more layers of the organic material layers include the compound of Chemical Formula 1.

The organic material layer of the organic light emitting device of the present invention can have a single-layer structure, or it can have a multilayered structure in which two or more organic material layers are stacked. For example, the organic light emitting device of the present invention can have a structure comprising a hole injection layer, a hole transport layer, a light emitting layer, an electron transport layer, an electron injection layer and the like as the organic material layer. However, the structure of the organic light emitting device is not limited thereto, and it can include a smaller number of organic layers.

Further, the organic material layer can include a hole injection layer, a hole transport layer, or a layer for simultaneously performing hole injection and transport, wherein the hole injection layer, the hole transport layer, or the layer for simultaneously performing hole injection and transport include the compound of Chemical Formula 1.

Further, the organic material layer can include a light emitting layer, wherein the light emitting layer includes the compound of Chemical Formula 1.

Further, the organic material layer can include an electron transport layer, or an electron n injection layer, wherein the electron transport layer, or the electron injection layer includes the compound of Chemical Formula 1.

Further, the electron transport layer, the electron injection layer, or the layer for simultaneously performing electron injection and electron transport includes the compound of Chemical Formula 1. In particular, the compound of Chemical Formula 1 according to one embodiment of the present invention has excellent thermal stability, a deep HOMO level of 6.0 eV or higher, high triplet energy (ET) and hole stability. Further, when using the compound of Chemical Formula 1 in an organic material layer performing electron injection and electron transfer at the same time, an n-type dopant used in the art can be mixed thereto.

Further, the organic material layer includes a light emitting layer and an electron transport layer, wherein the electron transport layer can include the compound of Chemical Formula 1.

Further, the organic light emitting device according to the present invention can be a normal type organic light emitting device in which an anode, one or more organic material layers and a cathode are sequentially stacked on a substrate. Further, the organic light emitting device according to the present invention can be an inverted type organic light emitting device in which a cathode, one or more organic material layers and an anode are sequentially stacked on a substrate. For example, the structure of an organic light emitting device according to an embodiment of the present disclosure is illustrated in FIGS. 1 and 2.

FIG. 1 shows an example of an organic light emitting device comprising a substrate 1, an anode 2, a light emitting layer 3, and a cathode 4. In such a structure, the compound of Chemical Formula 1 can be included in the light emitting layer.

FIG. 2 shows an example of an organic light emitting device comprising a substrate 1, an anode 2, a hole injection layer 5, a hole transport layer 6, a light emitting layer 7, an electron transport layer 8, and a cathode 4. In such a structure, the compound of Chemical Formula 1 can be included in one or more layers of the hole injection layer, the hole transport layer, the light emitting layer and the electron transport layer.

The organic light emitting device according to the present invention can be manufactured by materials and methods known in the art, except that one or more layers of the organic material layers include the compound of Chemical Formula 1. Moreover, when the organic light emitting device includes a plurality of organic material layers, the organic material layers can be formed of the same material or different materials.

For example, the organic light emitting device according to the present invention can be manufactured by sequentially stacking a first electrode, an organic material layer and a second electrode on a substrate. In this case, the organic light emitting device can be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer and the electron transport layer thereon, and then depositing a material that can be used as the cathode thereon. In addition to such a method, the organic light emitting device can be manufactured by sequentially depositing a cathode material, an organic material layer and an anode material on a substrate.

Further, the compound of Chemical Formula 1 can be formed into an organic layer by a solution coating method as well as a vacuum deposition method at the time of manufacturing an organic light emitting device. Herein, the solution coating method means a spin coating, a dip coating, a doctor blading, an inkjet printing, a screen printing, a spray method, a roll coating, or the like, but is not limited thereto.

In addition to such a method, the organic light emitting device can be manufactured by sequentially depositing a cathode material, an organic material layer and a an material anode on substrate (International Publication WO2003/012890). However, the manufacturing method is not limited thereto.

As an example, the first electrode is an anode, and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has a capability of transporting the holes, thus has a hole injecting effect in the anode and an excellent hole-injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrile hexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which can receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which can receive holes and electrons transported from a hole transport layer and an electron transport layer, respectively, and combine the holes and the electrons to emit light in a visible ray region, and has good quantum efficiency to fluorescence or phosphorescence. Specific examples thereof include an 8-hydroxy-quinoline aluminum complex ($Alq_3$); a carbazole-based compound; a dimerized styryl compound; BAlq; a 10-hydroxybenzoquinoline-metal compound; a benzoxazole, benzothiazole and benzimidazole-based compound; a poly(p-phenylenevinylene) (PPV)-based polymer; a spiro compound; polyfluorene, rubrene, and the like, but are not limited thereto.

The light emitting layer can include a host material and a dopant material. The host material can be a fused aromatic ring derivative, a heterocyclic-containing compound or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, e and the like, but are not limited thereto.

The dopant material can be an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene and the like, which have an arylamino group. The styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron transport layer is a layer which receives electrons from an electron injection layer and transports the electrons to a light emitting layer, and an electron transport material is suitably a material which can receive electrons well from a cathode and transfer the electrons to a light emitting layer and has large mobility for electrons. Specific examples thereof include: an Al complex of 8-hydroxyquinoline; a complex including Alq$_3$; an organic radical compound; a hydroxyflavone-metal complex, and the like, but are not limited thereto. The electron transport layer can be used with any desired cathode material, as used according to the related art. In particular, appropriate examples of the cathode material are a typical material which has a low work function, followed by an aluminum layer or a silver layer. Specific examples thereof include cesium, barium, calcium, ytterbium, and samarium, in each case followed by an aluminum layer or a silver layer.

The electron injection layer is a layer which injects electrons from an electrode, and is preferably a compound which has a capability of transporting electrons, has an effect of injecting electrons from a cathode and an excellent effect of injecting electrons into a light emitting layer or a light emitting material, prevents excitons produced from the light emitting layer from moving to a hole injection layer, and is also excellent in the ability to form a thin film. Specific examples thereof include fluorenone, anthraquinodimethane, diphenoquinone, thiopyran dioxide, oxazole, oxadiazole, triazole, imidazole, perylenetetracarboxylic acid, fluorenylidene methane, anthrone, and the like, and derivatives thereof, a metal complex compound, a nitrogen-containing 5-membered ring derivative, and the like, but are not limited thereto.

Examples of the metal complex compound include 8-hydroxyquinolinato lithium, bis(8-hydroxyquinolinato) zinc, bis(8-hydroxyquinolinato) copper, bis(8-hydroxyquinolinato) manganese, tris(8-hydroxyquinolinato)aluminum, tris(2-methyl-8-hydroxyquinolinato)aluminum, tris(8-hydroxyquinolinato)-gallium, bis(10-hydroxybenzo[h]quinolinato) beryllium, bis(10-hydroxybenzo[h]quinolinato) zinc, bis(2-methyl-8-quinolinato)chlorogallium, bis(2-methyl-8-quinolinato) (o-cresolato) gallium, bis(2-methyl-8-quinolinato) (1-naphtholato)aluminum, bis(2-methyl-8-quinolinato) (2-naphtholato) gallium, and the like, but are not limited thereto.

The organic light emitting device according to the present invention can be a front side emission type, a backside emission type, or a double-sided emission type according to the used material.

In addition, the compound of Chemical Formula 1 can be included in an organic solar cell or an organic transistor in addition to an organic light emitting device.

The preparation of the compound of Chemical Formula 1 and the organic light emitting device containing the same will be described in detail in the following examples. However, these examples are presented for illustrative purposes only and are not intended to limit the scope of the present invention.

PREPARATION EXAMPLE

Preparation Example 1: Preparation of Compound 1

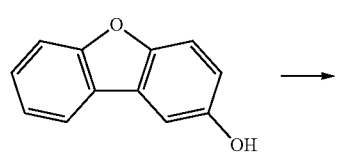

-continued

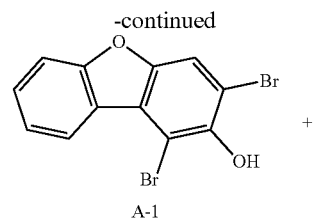
A-1

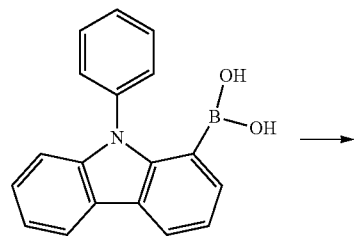

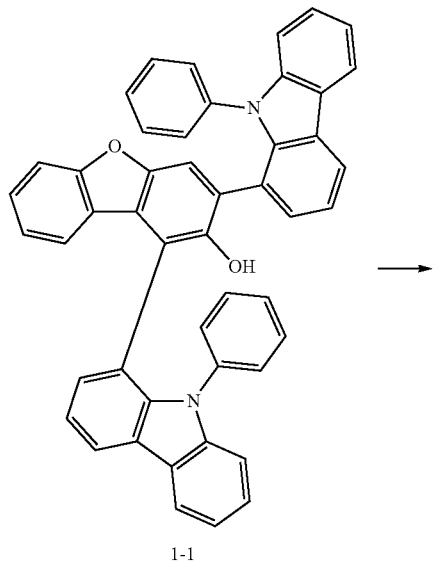
1-1

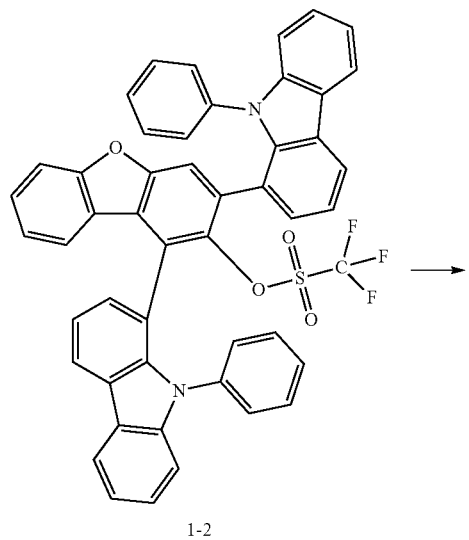
1-2

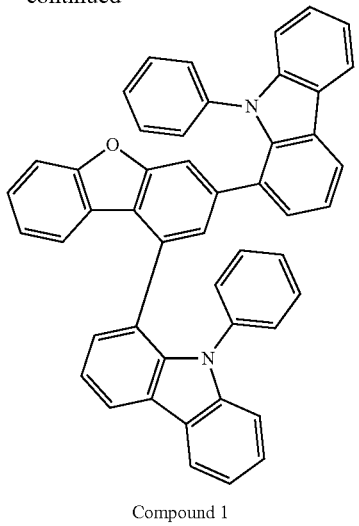

Compound 1

1) Synthesis of Compound A-1

Dibenzo[b,d]furan-2-ol (30 g, 163.0 mmol) was dissolved in 300 ml of chloroform. N-bromosuccinimide (58.0 g, 326.0 mmol) was added thereto and stirred at room temperature for 4 h. After the reaction was completed, water was added. After layer separation, the mixture was stirred twice with sodium thiosulfate solution, and then the layers were separated. Then, it was distillated to give Compound A-1 (31.6 g, 79%).

MS: [M+H]+=341

2) Synthesis of Compound 1-1

Under a nitrogen atmosphere, Compound A1 (20.0 g, 58.9 mmol) and (9-phenyl-9H-carbazol-1-yl) boronic acid (33.8 g, 117.7 mmol) were added to 300 ml of tetrahydrofuran and the mixture was stirred and refluxed. Thereafter, potassium carbonate (48.8 g, 353.1 mmol) was dissolved in and added to 100 ml of water and sufficiently stirred, then tetrakistriphenyl-phosphinopalladium (4.1 g, 6 mol %) was added thereto. After the reaction for 12 hours, the temperature was lowered to room temperature, the organic layer and the aqueous layer were separated, and the organic layer was distilled under reduced pressure. The distillate was extracted with chloroform and water, and then the organic layer was dried over magnesium sulfate. Then, the organic layer was dried and recrystallized with ethanol to give Compound 1-1 (23.9 g, 61%).

MS: [M+H]+=667

3) Synthesis of Compound 1-2

After Compound 1-1 (23.9 g, 35.9 mmol) was dissolved in 300 ml of acetonitrile under a nitrogen atmosphere, potassium carbonate (9.9 g, 71.8 mmol) was added thereto and then stirred for about 30 minutes. Then, trifluoromethanesulfonyl chloride (9.0 g, 53.8 mmol) was slowly added. After the reaction for 12 hours, layer and the aqueous layer were separated, and then the organic layer was distilled under reduced pressure. The distillate was extracted with chloroform and water, and then the organic layer was dried over magnesium sulfate. Then, the organic layer was dried and recrystallized with ethanol to give Compound 1-2 (24.1 g, 84%).

MS: [M+H]=798

3) Synthesis of Compound 1

Under a nitrogen atmosphere, Compound 1-2 (24.1 g, 30.2 mmol) was added to 300 ml of tetrahydrofuran and 50 ml of ethanol, and the mixture was stirred and refluxed. Then, potassium carbonate (12.5 g, 90.5 mmol) was dissolved in and added to 100 ml of water and sufficiently stirred, then tetrakistriphenyl-phosphinopalladium (1.0 g, 3 mol %) was added thereto. After the reaction for 12 hours, the temperature was lowered to room temperature, the organic layer and the aqueous layer were separated, and then the organic layer was distilled under reduced pressure. The distillate was extracted with chloroform and water, and then the organic layer was dried over magnesium sulfate. Then, the organic layer was dried and recrystallized with ethyl acetate to give Compound 1 (8.0 g, 41%) as a white solid.

MS: [M+H]+=651

Preparation Example 2: Preparation of Compound 2

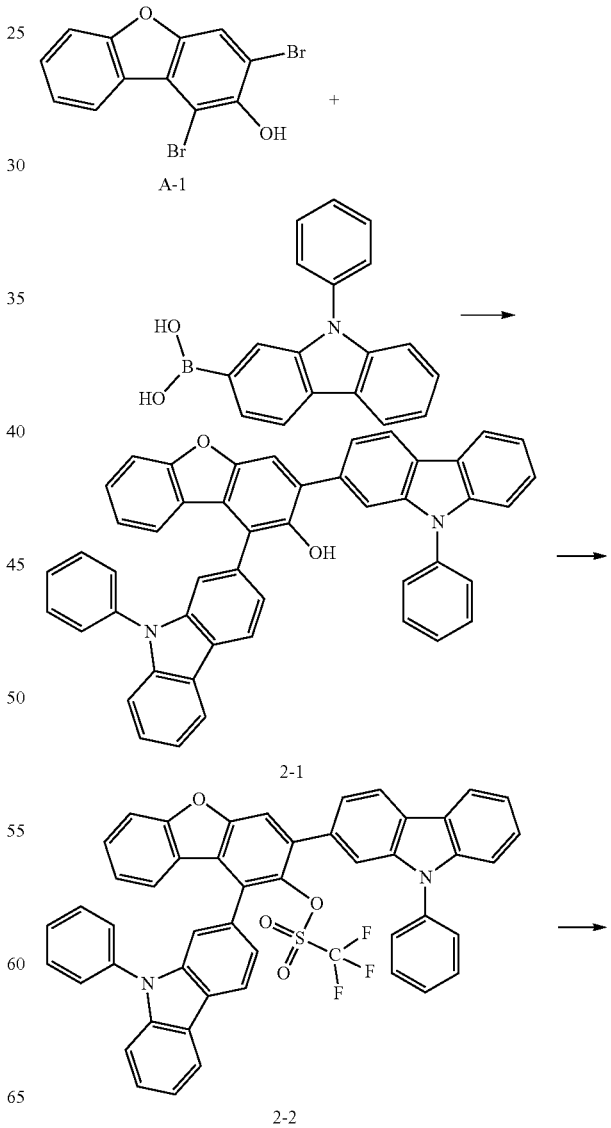

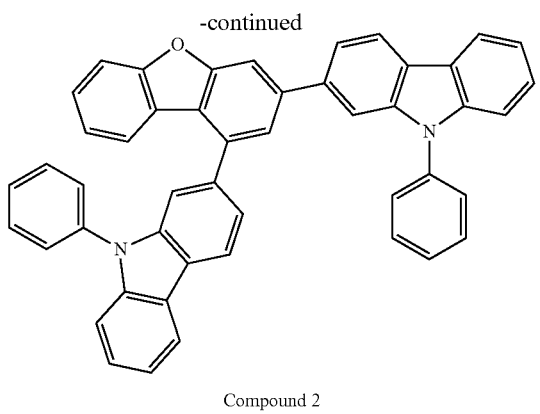

Compound 2

1) Synthesis of Compound 2-1

Under a nitrogen atmosphere, Compound A1 (20.0 g, 58.9 mmol) and (9-phenyl-9H-carbazol-2-yl) boronic acid (33.8 g, 117.7 mmol) were added to 300 ml of tetrahydrofuran and the mixture was stirred and refluxed. Then, potassium carbonate (48.8 g, 353.1 mmol) was dissolved in and added to 100 ml of water, stirred sufficiently, and then tetrakistriphenyl-phosphinopalladium (4.1 g, 6 mol %) was added thereto. After the reaction for 12 hours, the temperature was lowered to room temperature, the organic layer and the aqueous layer were separated, and then the organic layer was distilled under reduced pressure. The distillate was extracted with chloroform and water, then the organic layer was dried over magnesium sulfate. Then, the organic layer was dried and recrystallized with ethanol to give Compound 2-1 (30.2 g, 77%).

MS: [M+H]+=667

3) Synthesis of Compound 2-2

After Compound 2-1 (30.2 g, 45.3 mmol) was dissolved in 300 ml of acetonitrile under a nitrogen atmosphere, potassium carbonate (12.5 g, 90.6 mmol) was added thereto and then stirred for about 30 minutes. Then, trifluoromethanesulfonyl chloride (11.4 g, 67.9 mmol) was slowly added. After the reaction for 12 hours, water was added to complete the reaction, the organic layer and the aqueous layer were separated, and then the organic layer was distilled under reduced pressure. The distillate was extracted with chloroform and water, and then the organic layer was dried over magnesium sulfate. Then, the organic layer was dried and recrystallized with ethanol to give Compound 2-2 (32.2 g, 89%).

MS: [M+H]=798

3) Synthesis of Compound 2

Under a nitrogen atmosphere, Compound 2-2 (32.2 g, 40.3 mmol) was added to 300 ml of tetrahydrofuran and 50 ml of ethanol, and the mixture was stirred and refluxed. Then, potassium carbonate (16.7 g, 120.9 mmol) was dissolved in and added to 100 ml of water and sufficiently stirred, then tetrakistriphenyl-phosphinopalladium (1.4 g, 3 mol %) was added thereto. After the reaction for 12 hours, the temperature was lowered to room temperature, the organic layer and the aqueous layer were separated, and then the organic layer was distilled under reduced pressure. The distillate was extracted with chloroform and water, and then the organic layer was dried over magnesium sulfate. Then, the organic layer was dried and recrystallized with ethyl acetate to give Compound 2 (13.4 g, 51%) as a white solid.

MS: [M+H]+=651

Preparation Example 3: Preparation of Compound 3

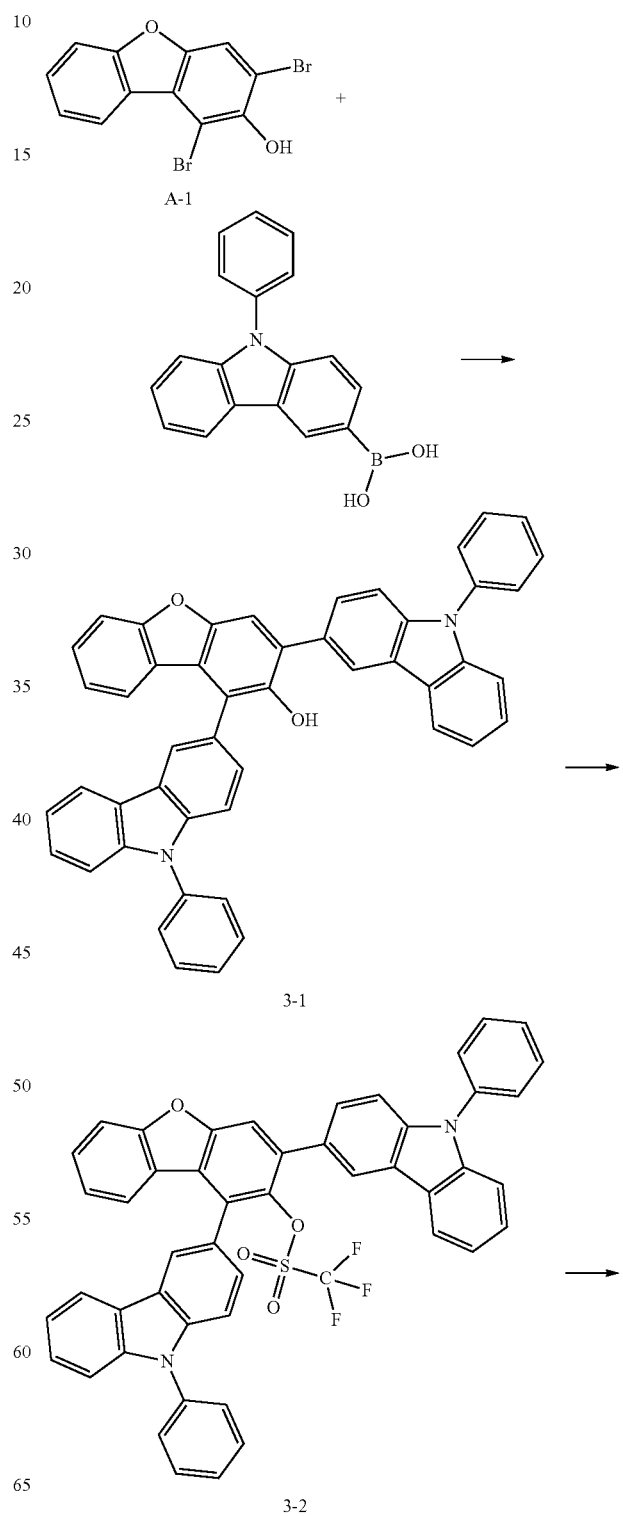

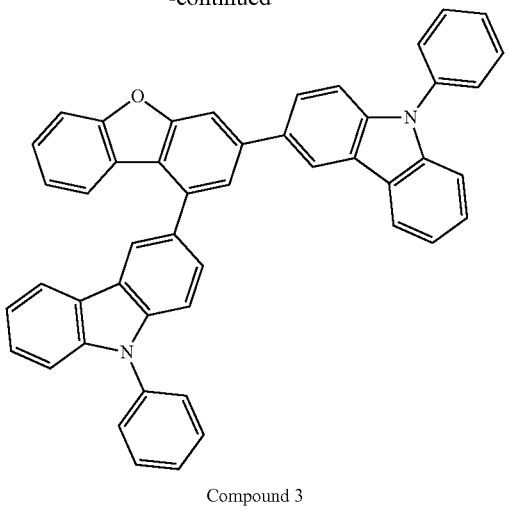

Compound 3

1) Synthesis of Compound 3-1

Under a nitrogen atmosphere, Compound A1 (20.0 g, 58.9 mmol) and (9-phenyl-9H-carbazol-3-yl) boronic acid (33.8 g, 117.7 mmol) were added to 300 ml of tetrahydrofuran, and the mixture was stirred and refluxed. Then, potassium carbonate (48.8 g, 353.1 mmol) was dissolved in and added to 100 ml of water and sufficiently stirred, then tetrakistriphenyl-phosphinopalladium (4.1 g, 6 mol %) was added thereto. After the reaction for 12 hours, the temperature was lowered to room temperature, the organic layer and the aqueous layer were separated, and then the organic layer was distilled under reduced pressure. The distillate was extracted with chloroform and water, and then the organic layer was dried over magnesium sulfate. Then, the organic layer was dried and recrystallized with ethanol to give Compound 3-1 (23.1 g, 59%).

MS: [M+H]+=667

2) Synthesis of Compound 3-2

After Compound 3-1 (23.1 g, 34.7 mmol) was dissolved in 300 ml of acetonitrile under a nitrogen atmosphere, potassium carbonate (9.6 g, 69.4 mmol) was added thereto and then stirred for about 30 minutes. Then, trifluoromethanesulfonyl chloride (8.7 g, 52.1 mmol) was slowly added. After the reaction for 12 hours, water was added to complete the reaction, the organic layer and the aqueous layer were separated, and then the organic layer was distilled under reduced pressure. The distillate was extracted with chloroform and water, and then the organic layer was dried over magnesium sulfate. Then, the organic layer was dried and recrystallized with ethanol to give Compound 3-2 (25.2 g, 91%).

MS: [M+H]=798

3) Synthesis of Compound 3-3

Under a nitrogen atmosphere, Compound 3-2 (25.2 g, 31.6 mmol) was added to 300 ml of tetrahydrofuran and 50 ml of ethanol, and the mixture was stirred and refluxed. Then, potassium carbonate (13.1 g, 94.8 mmol) was dissolved in and added to 100 ml of water and sufficiently stirred, then tetrakistriphenyl-phosphinopalladium (1.1 g, 3 mol %) was added thereto. After the reaction for 12 hours, the temperature was lowered to room temperature, the organic layer and the aqueous layer were separated, and then the organic layer was distilled under reduced pressure. The distillate was extracted with chloroform and water, and then the organic layer was dried over magnesium sulfate. Then, the organic layer was dried and recrystallized with ethyl acetate to give Compound 3 (13.1 g, 64%) as a white solid.

MS: [M+H]+=651

Preparation Example 4: Preparation of Compound 4

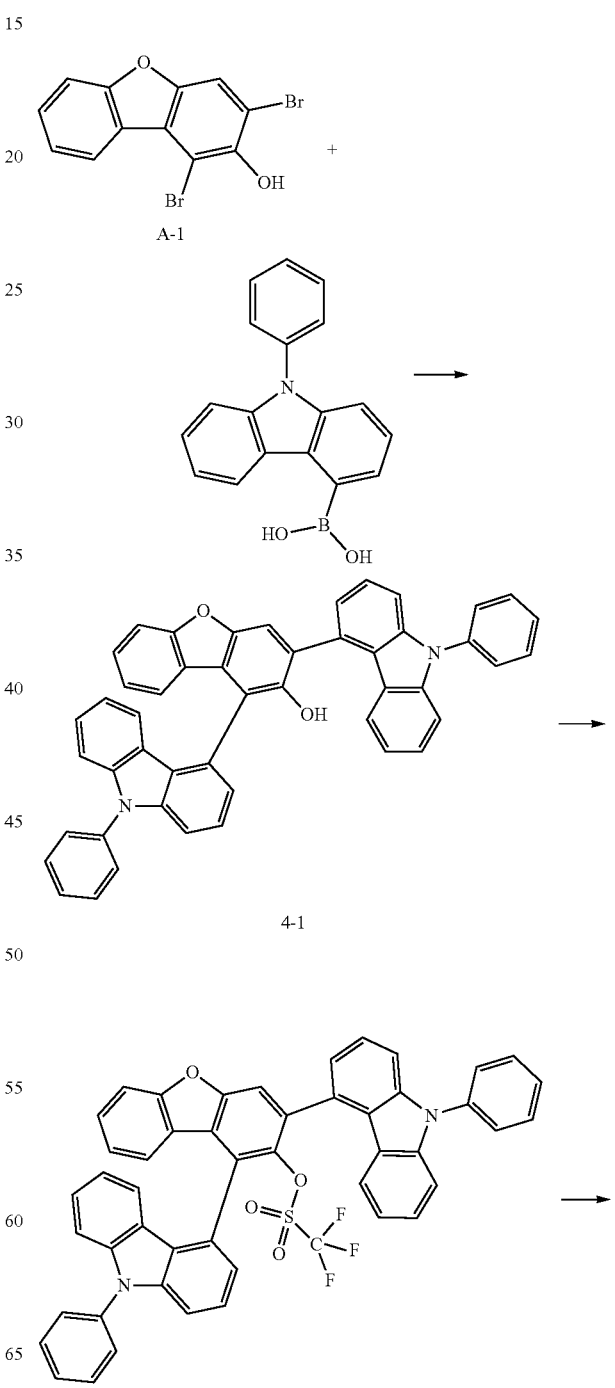

-continued

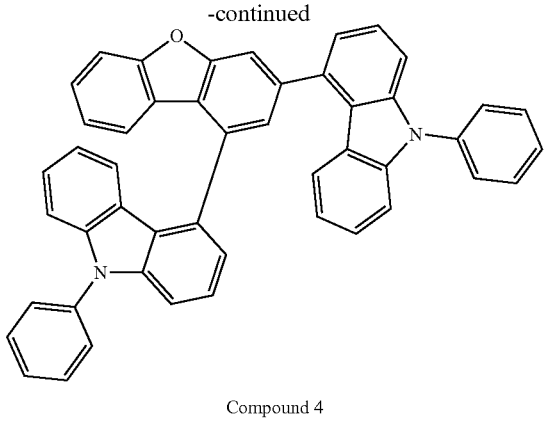

Compound 4

1) Synthesis of Compound 4-1

Under a nitrogen atmosphere, Compound A1 (20.0 g, 58.9 mmol) and (9-phenyl-9H-carbazol-4-yl) boronic acid (33.8 g, 117.7 mmol) were added to 300 ml of tetrahydrofuran, and the mixture was stirred and refluxed. Then, potassium carbonate (48.8 g, 353.1 mmol) was dissolved in and added to 100 ml of water and sufficiently stirred, then tetrakistriphenyl-phosphinopalladium (1.1 g, 6 mol %) was added thereto. After the reaction for 12 hours, the temperature was lowered to room temperature, the organic layer and the aqueous layer were separated, and then the organic layer was distilled under reduced pressure. The distillate was extracted with chloroform and water, and then the organic layer was dried over magnesium sulfate. Then the organic layer was dried and recrystallized with ethanol to give Compound 4-1 (24.7 g, 63%).

MS: [M+H]+=667

2) Synthesis of Compound 4-2

After Compound 4-1 (24.7 g, 58.9 mmol) was dissolved in 300 ml of acetonitrile under a nitrogen atmosphere, potassium carbonate (10.2 g, 74.2 mmol) was added thereto and then stirred for about 30 minutes. Then, trifluoromethanesulfonyl chloride (9.3 g, 55.5 mmol) was slowly added. After the reaction for 12 hours, layer and the aqueous layer were separated, and then the organic layer was distilled under reduced pressure. The distillate was extracted with chloroform and water, and then the organic layer was dried over magnesium sulfate. Then, the organic layer was dried and recrystallized with ethanol to give Compound 4-2 (26.0 g, 88%).

MS: [M+H]=798

3) Synthesis of Compound 4

Under a nitrogen atmosphere, Compound 4-2 (26.0 g, 32.6 mmol) was added to 300 ml of tetrahydrofuran and 50 ml of ethanol, and the mixture was stirred and refluxed. Then, potassium carbonate (13.5 g, 97.9 mmol) was dissolved in and added to 100 ml of water and sufficiently stirred, then tetrakistriphenyl-phosphinopalladium (1.1 g, 3 mol %) was added thereto. After the reaction for 12 hours, the temperature was lowered to room temperature, the organic layer and the aqueous layer were separated, and then the organic layer was distilled under reduced pressure. The distillate was extracted with chloroform and water, and then the organic layer was dried over magnesium sulfate. Then, the organic layer was dried and recrystallized with ethyl acetate to give Compound 4 (10.6 g, 50%) as a white solid.

MS: [M+H]+=651

Preparation Example 5: Preparation of Compound 5

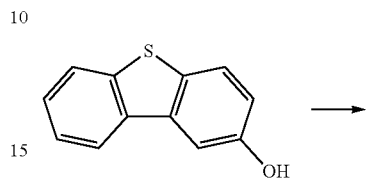

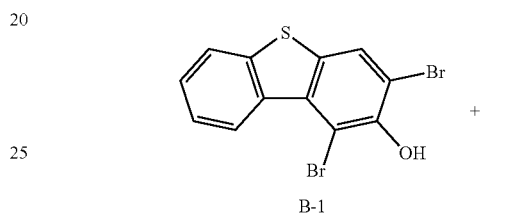

B-1

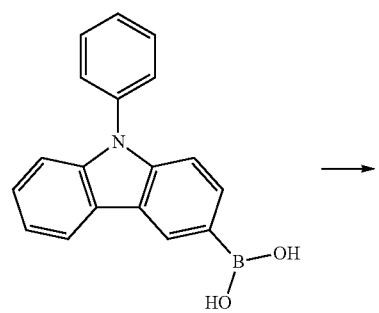

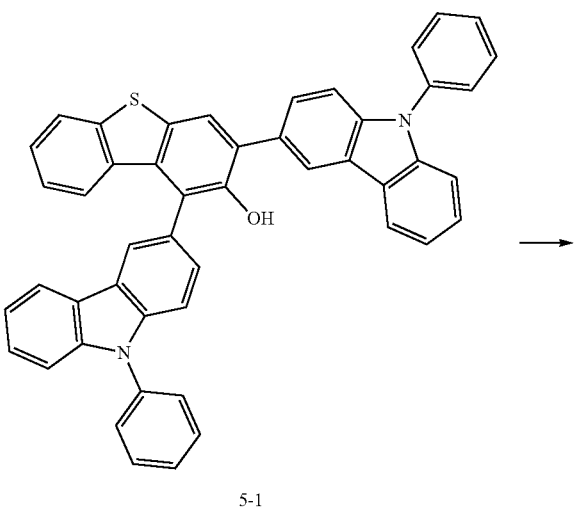

5-1

-continued

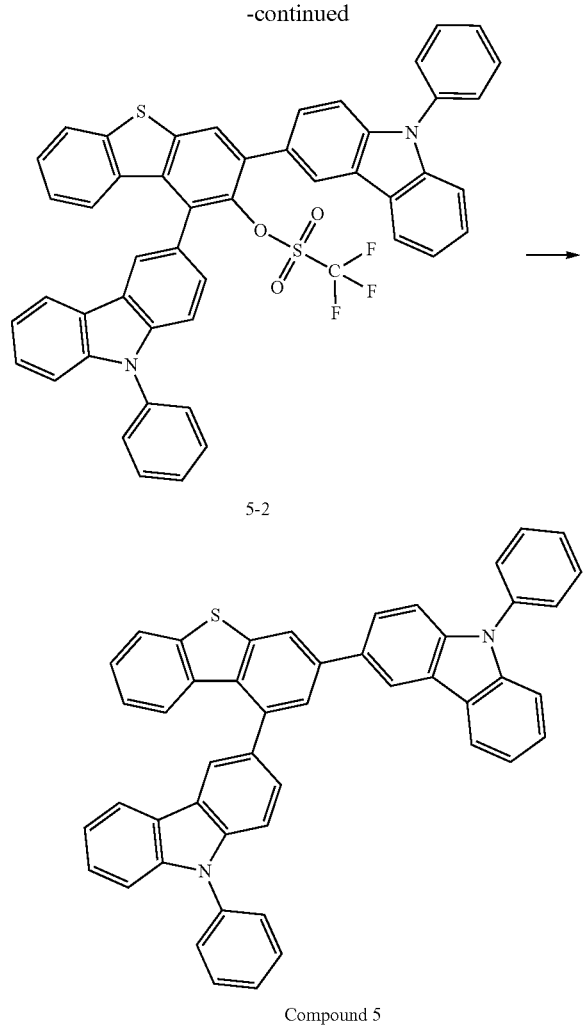

5-2

Compound 5

1) Synthesis of Compound B-1

Dibenzo[b,d]furan-2-ol (30 g, 150.0 mmol) was dissolved in 300 ml of chloroform. N-bromosuccinimide (53.4 g, 235.2 mmol) was added thereto and stirred at room temperature for 4 h. After the reaction was completed, water was added. After layer separation, the mixture was stirred twice with sodium thiosulfate solution, and the layers were separated. Then, it was distillated to give Compound B-1 (44.8 g, 84%).

MS: [M+H]+=357

2) Synthesis of Compound 5-1

Under a nitrogen atmosphere, Compound B1 (20.0 g, 56.2 mmol) and (9-phenyl-9H-carbazol-1-yl) boronic acid (32.3 g, 112.4 mmol) were added to 300 ml of tetrahydrofuran and the mixture was stirred and refluxed. Thereafter, carbonate (46.6 g, 337.2 mmol) was dissolved in and added to 100 ml of water and sufficiently stirred, then tetrakistriphenyl-phosphinopalladium (3.9 g, 6 mol %) was added thereto. After the reaction for 12 hours, the temperature was lowered to room temperature, the organic layer and the aqueous layer were separated, and the organic layer was distilled under reduced pressure. The distillate was extracted with chloroform and water, and then the organic layer was dried over magnesium sulfate. Then, the organic layer was dried and recrystallized with ethanol to give Compound 5-1 (29.5 g, 77%).

MS: [M+H]+=683

3) Synthesis of Compound 5-2

After Compound 5-1 (29.5 g, 43.3 mmol) was dissolved in 300 ml of acetonitrile under a nitrogen atmosphere, potassium carbonate (12.0 g, 86.6 mmol) was added thereto and then stirred for about 30 minutes. Then, trifluoromethanesulfonyl chloride (10.9 g, 64.9 mmol) was slowly added. After the reaction for 12 hours, layer and the aqueous layer were separated, and the organic layer was distilled under reduced pressure. The distillate was extracted with chloroform and water, and then the organic layer was dried over magnesium sulfate. Then, the organic layer was dried and recrystallized with ethanol to give Compound 5-2 (31.0 g, 88%).

MS: [M+H]=812

3) Synthesis of Compound 5

Under a nitrogen atmosphere, Compound 5-2 (31.0 g, 38.1 mmol) was added to 300 ml of tetrahydrofuran and 50 ml of ethanol, and the mixture was stirred and refluxed. Then, potassium carbonate (15.8 g, 114.3 mmol) was dissolved in and added to 100 ml of water and sufficiently stirred, then tetrakistriphenyl-phosphinopalladium (1.3 g, 3 mol %) was added thereto. After the reaction for 12 hours, the temperature was lowered to room temperature, the organic layer and the aqueous layer were separated, and then the organic layer was distilled under reduced pressure. The distillate was extracted with chloroform and water, and then the organic layer was dried over magnesium sulfate. Then, the organic layer was dried and recrystallized with ethyl acetate to give Compound 5 (15.2 g, 60%) as a white solid.

MS: [M+H]+=667

Preparation Example 6: Preparation of Compound 6

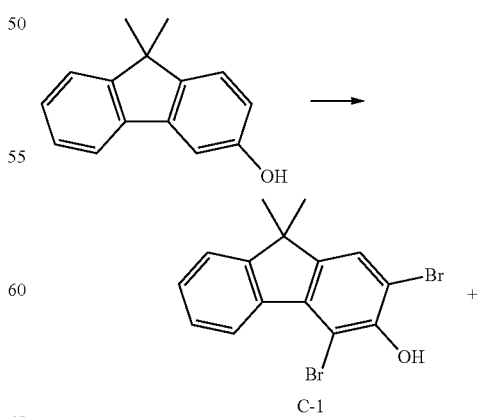

C-1

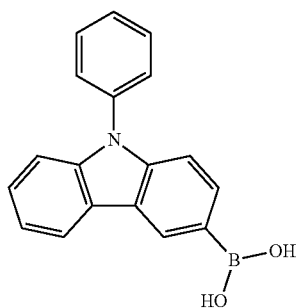
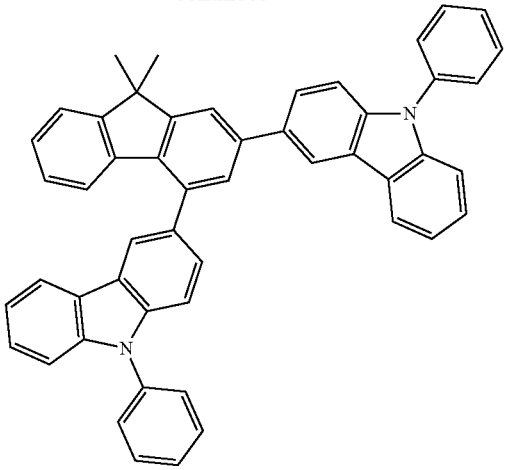

Compound 6

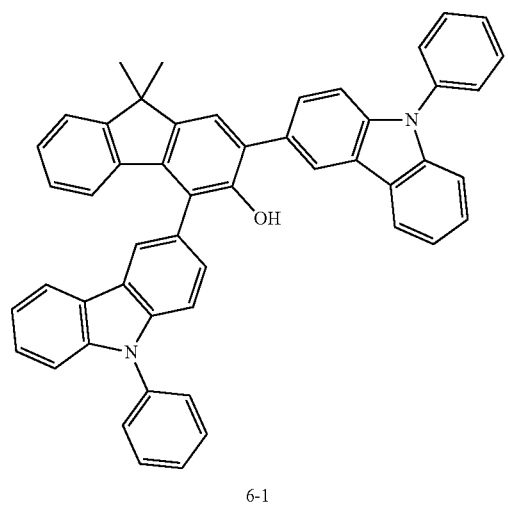 [SMILES: c1ccc(-n2c3ccccc3c3cc(-c4cc(-c5ccc6c(c5)c5ccccc5n6-c5ccccc5)c5c(c4)oc4ccccc45)ccc32)cc1]

6-1

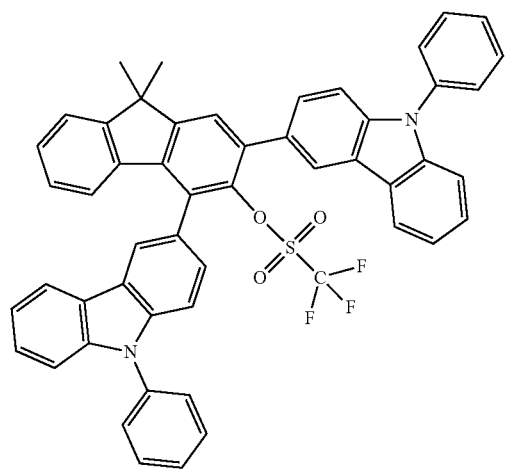

6-2

1) Synthesis of Compound C-1

9,9-Dimethyl-9H-fluoren-3-ol (30 g, 142.8 mmol) was dissolved in 300 ml of chloroform. N-bromosuccinimide (53.4 g, 235.2 mmol) was added thereto and stirred at room temperature for 4 h. After the reaction was completed, water was added. After layer separation, the mixture was stirred twice with sodium thiosulfate solution, and the layers were separated. Then, it was distillated to give Compound C-1 (34.5 g, 66%).

MS: [M+H]+=367

2) Synthesis of Compound 6-1

Under a nitrogen atmosphere, Compound C-1 (20.0 g, 54.7 mmol) and (9-phenyl-9H-carbazol-3-yl) boronic acid (31.4 g, 109.3 mmol) were added to 300 ml of tetrahydrofuran and the mixture was stirred and refluxed. Thereafter, potassium carbonate (45.3 g, 327.9 mmol) was dissolved in and added to 100 ml of water and sufficiently stirred, then tetrakistriphenyl-phosphinopalladium (3.8 g, 6 mol %) was added thereto. After the reaction for 12 hours, the temperature was lowered to room temperature, the organic layer and the aqueous layer were separated, and the organic layer was distilled under reduced pressure. The distillate was extracted with chloroform and water, and then the organic layer was dried over magnesium sulfate. Then, the organic layer was dried and recrystallized with ethanol to give Compound 6-1 (20.4 g, 54%).

MS: [M+H]+=693

3) Synthesis of Compound 6-2

After Compound 6-1 (20.4 g, 30.0 mmol) was dissolved in 300 ml of acetonitrile under a nitrogen atmosphere, potassium carbonate (8.3 g, 59.9 mmol) was added thereto and then stirred for about 30 minutes. Then, trifluoromethanesulfonyl chloride (7.5 g, 44.9 mmol) was slowly added. After the reaction for 12 hours, layer and the aqueous layer were separated, and the organic layer was distilled under reduced pressure. The distillate was extracted with chloroform and water, and then the organic layer was dried over magnesium sulfate. Then, the organic layer was dried and recrystallized with ethanol to give Compound 6-2 (14.6 g, 59%).

MS: [M+H]=825

3) Synthesis of Compound 6

Under a nitrogen atmosphere, Compound 6-2 (14.6 g, 17.9 mmol) was added to 300 ml of tetrahydrofuran and 50 ml of ethanol, and the mixture was stirred and refluxed. Then, potassium carbonate (7.4 g, 53.7 mmol) was dissolved in and added to 100 ml of water and sufficiently stirred, then tetrakistriphenyl-phosphinopalladium (0.6 g, 3 mol %) was added thereto. After the reaction for 12 hours, the temperature was lowered to room temperature, the organic layer and the aqueous layer were separated, and then the organic layer was distilled under reduced pressure. The distillate was extracted with chloroform and water, and then the organic layer was dried over magnesium sulfate. Then, the organic layer was dried and recrystallized with ethyl acetate to give Compound 6 (7.0 g, 58%) as a while solid.

MS: [M+H]+=667

EXPERIMENTAL EXAMPLES

Experimental Example 1

A glass substrate on which ITO (indium tin oxide) was coated as a thin film to a thickness of 1, 300 Å was put into distilled water in which a detergent was dissolved, and ultrasonically cleaned. A product manufactured by Fischer Co. was used as the detergent, and as the distilled water, distilled water filtered twice using a filter manufactured by Millipore Co. was used. After the ITO was s cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, dried, and then transferred to a plasma cleaner. The substrate was cleaned for 5 minutes using oxygen plasma and then transferred to a vacuum depositor.

On the ITO transparent electrode thus prepared, the following compound HI-1 was thermally vacuum-deposited to a thickness of 50 Å to form a hole injection layer. The following compound HT-1 was thermally vacuum-deposited on the hole injection layer to a thickness of 250 Å to form a hole transport layer, and the following compound HT-2 was vacuum-deposited on the HT-1 deposited layer to a thickness of 50 Å to form an electron blocking layer. The compound 1 prepared in the previous Preparation Example 1, the following compound YGH-1, and a phosphorescent dopant YGD-1 were co-deposited in a weight ratio of 44:44:12 on the HT-2 deposited layer to form a light emitting layer with a thickness of 400 Å. The following compound ET-1 was vacuum-deposited on the light emitting layer to a thickness of 250 Å to form an electron transport layer, and the following compound ET-2 and Li were vacuum-deposited in a weight ratio of 98:2 on the electron transport layer to form an electron injection layer with a thickness of 100 Å. Aluminum was deposited on the electron injection layer to a thickness of 1000 Å to form a cathode.

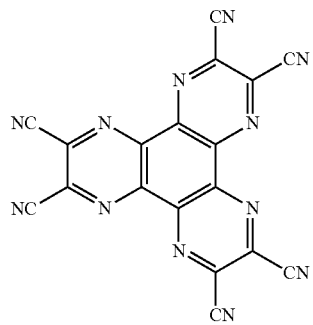

HI-1

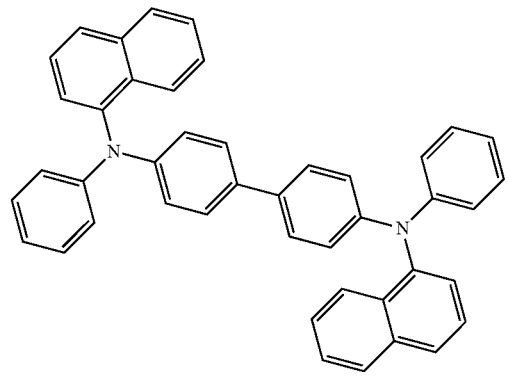

HT-1

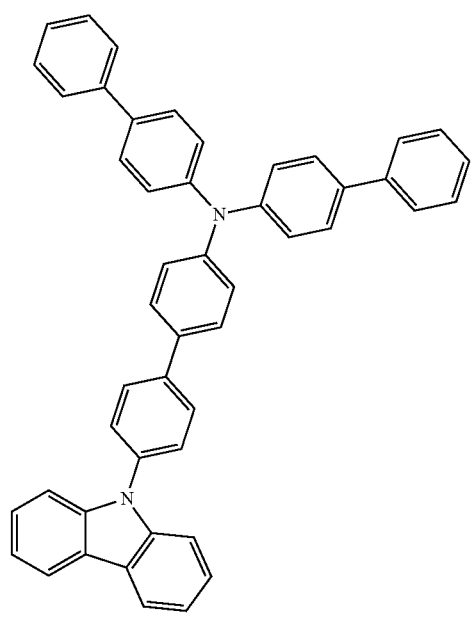

HT-2

-continued

YGH-1
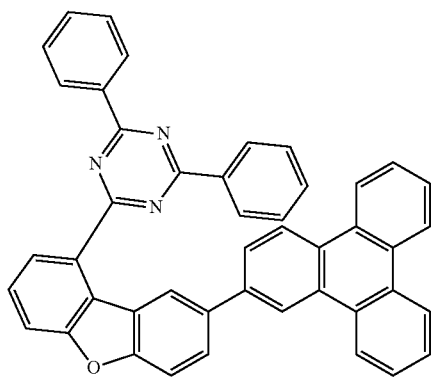

YGD-1
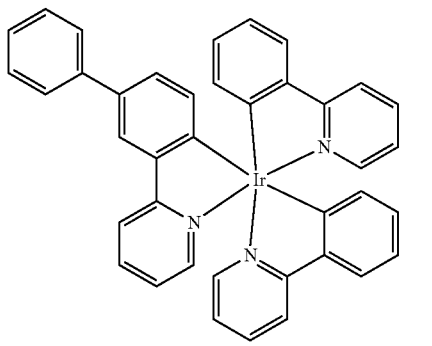

ET-1
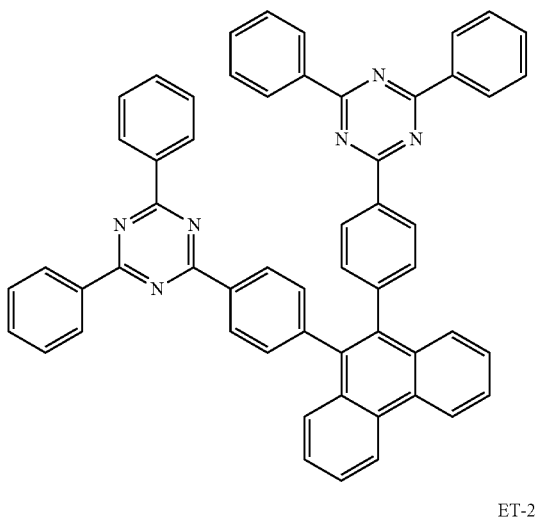

ET-2
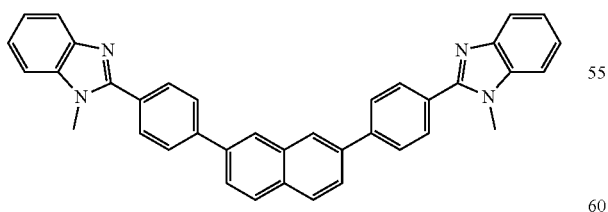

In the above-mentioned process, the vapor deposition rate of the organic material was maintained at 0.4 to 0.7 Å/sec, the deposition rate of aluminum was maintained at 2 Å/sec, and the degree of vacuum during the deposition was maintained at $1 \times 10^{-7}$ to $5 \times 10^{-8}$ torr.

Experimental Examples 2 to 6

An organic light emitting device was manufactured in the same manner as in Experimental Example 1, except that the compounds shown in Table 1 below were used instead of Compound 1 of Preparation Example 1 in Experimental Example 1.

Comparative Experimental Examples 1 to 3

An organic light emitting device was manufactured in the same manner as in Experimental Example 1, except that the compounds shown in Table 1 below were used instead of Compound 1 of Preparation Example 1 in Experimental Example 1. The compounds of CE1 to CE3 shown in Table 1 are as follows.

CE 1
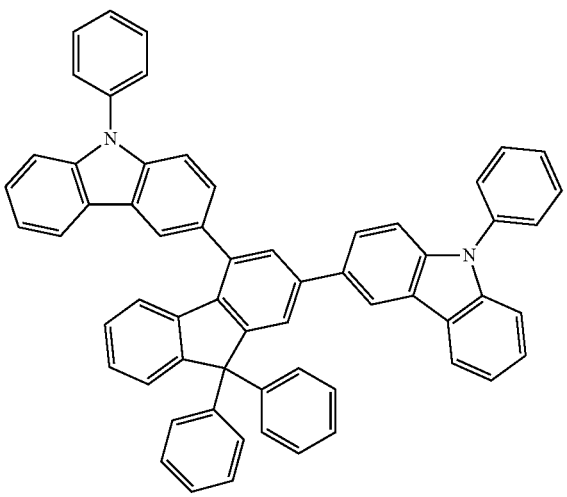

CE 2
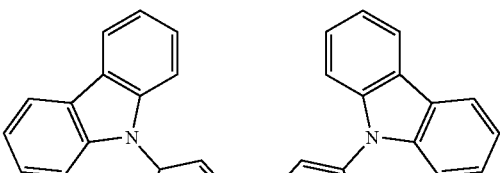
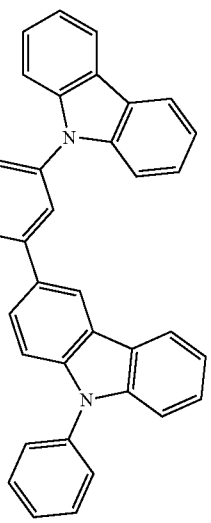

-continued

CE 3

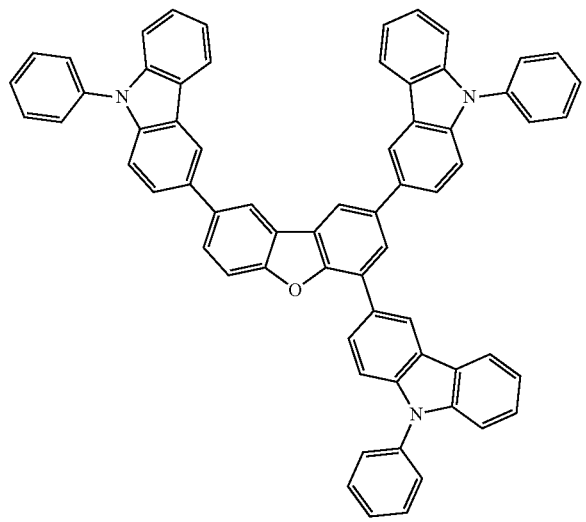

For the organic light emitting devices manufactured in Experimental Examples and Comparative Experimental Examples, the voltage and efficiency were measured at a current density of 10 mA/cm² and the lifetime was measured at a current density of 50 mA/cm². The results are shown in Table 1 below. In this case, $LT_{95}$ means the time required for the luminance to be reduced to 95% of the initial luminance.

TABLE 1

| Category | Compound | Voltage (V) (@10 mA/cm²) | Efficiency (Cd/A) (@10 mA/cm²) | Color coordinate (x, y) | Lifetime (h) ($LT_{95}$ at 50 mA/cm²) |
|---|---|---|---|---|---|
| Experimental Example 1 | Compound 1 | 4.4 | 83 | 0.44, 0.54 | 140 |
| Experimental Example 2 | Compound 2 | 4.3 | 83 | 0.46, 0.54 | 160 |
| Experimental Example 3 | Compound 3 | 4.2 | 81 | 0.46, 0.55 | 170 |
| Experimental Example 4 | Compound 4 | 4.3 | 82 | 0.46, 0.54 | 160 |
| Experimental Example 5 | Compound 5 | 4.3 | 80 | 0.46, 0.54 | 180 |
| Experimental Example 6 | Compound 6 | 4.5 | 81 | 0.46, 0.54 | 140 |
| Comparative Experimental Example 1 | CE1 | 4.6 | 76 | 0.46, 0.54 | 85 |
| Comparative Experimental Example 2 | CE2 | 4.5 | 75 | 0.47, 0.54 | 95 |
| Comparative Experimental Example 3 | CE3 | 4.9 | 76 | 0.48, 0.59 | 100 |

As shown in Table 1, it was confirmed that when the compound of the present invention was used as an organic light emitting layer material, it exhibited excellent characteristics in terms of efficiency and as compared with Comparative Experimental lifetime Examples. This confirms that the compound of the present invention has a specific core structure and two carbazoles are substituted at positions 1 and 3, thereby increasing the electron and hole stability.

DESCRIPTION OF SYMBOLS

1: substrate
2: anode
3: light emitting layer
4: cathode
5: hole injection layer
6: hole transport layer
7: light emitting layer
8: electron transport layer

The invention claimed is:

1. A compound of Chemical Formula 1:

Chemical Formula 1

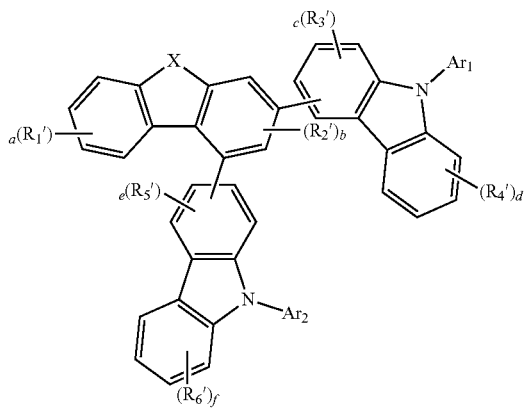

wherein, in Chemical Formula 1:

X is O, S, or $C(R_1R_2)$;

$R_1$ and $R_2$ are each independently a substituted or unsubstituted $C_{1-60}$ alkyl;

$Ar_1$ and $Ar_2$ are each independently any one selected from the group consisting of the following:

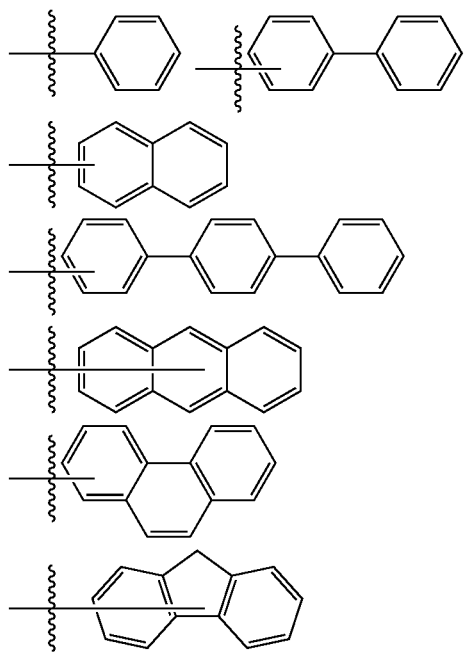

-continued

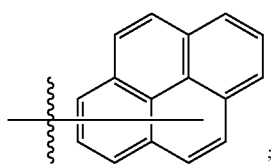

$R_1'$ and $R_2'$ are each independently hydrogen, deuterium, halogen, cyano, nitro, amino, or a substituted or unsubstituted $C_{1-60}$ alkyl;

$R_3'$, $R_4'$, $R_5'$, and $R_6'$ are each independently hydrogen, deuterium, halogen, cyano, nitro, amino, or a substituted or unsubstituted $C_{1-60}$ alkyl;

a, d, and f are each independently an integer of 0 to 4;

b is an integer of 0 to 2; and c and e are each independently an integer of 0 to 3.

2. The compound according to claim 1, wherein $R_1$ and $R_2$ are each independently methyl, ethyl or propyl.

3. The compound according to claim 1, wherein $Ar_1$ and $Ar_2$ are each independently

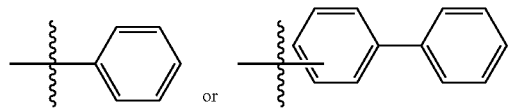

4. The compound according to claim 1, wherein the compound of Chemical Formula 1 is any one compound selected from the group consisting of the following compounds:

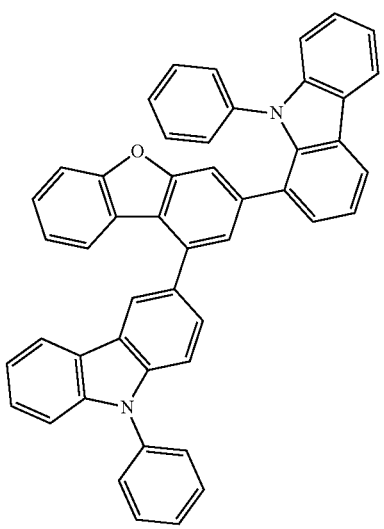

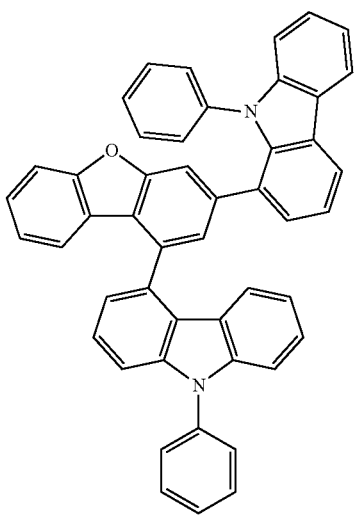

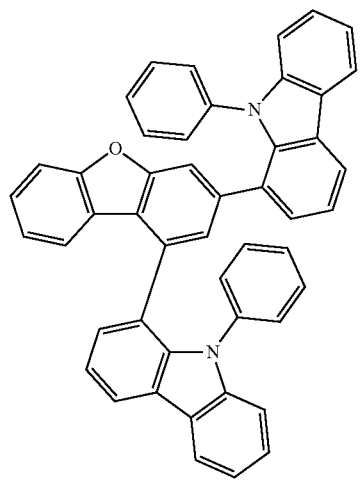

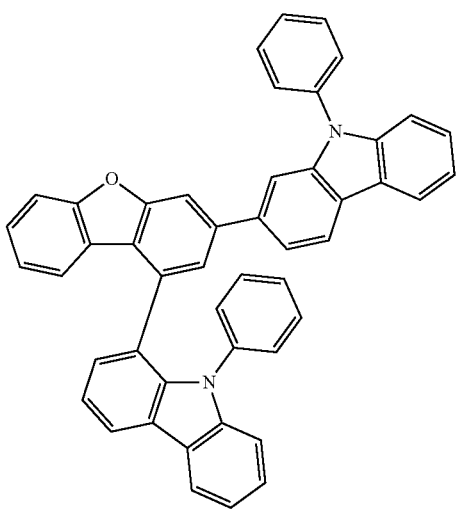

53
-continued
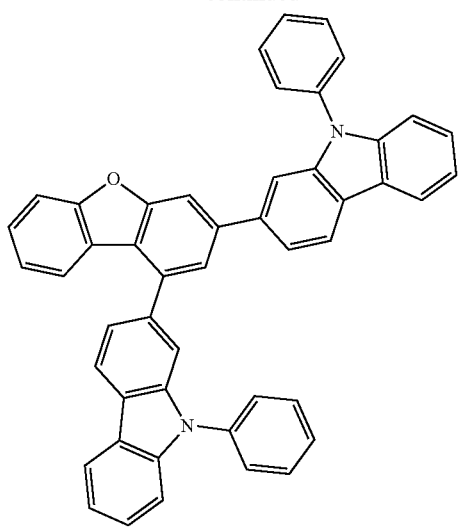
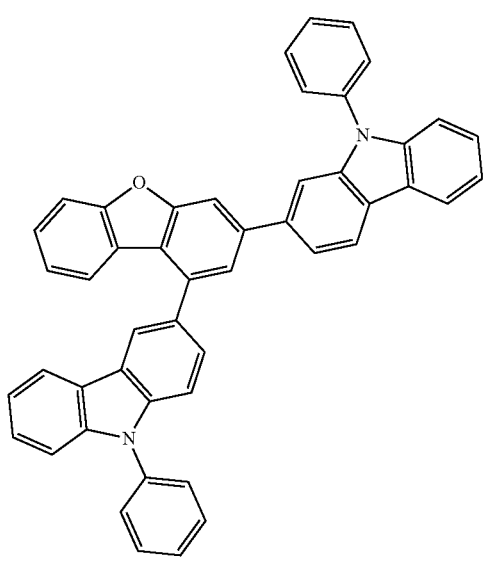
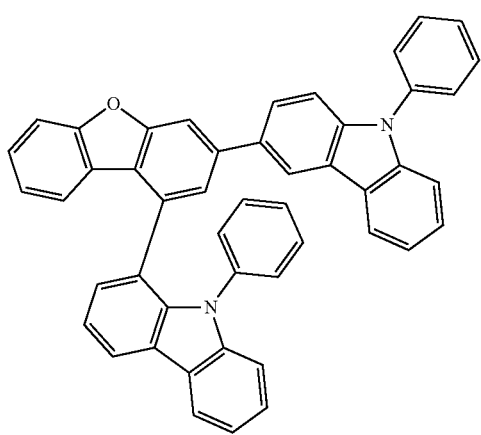
54
-continued
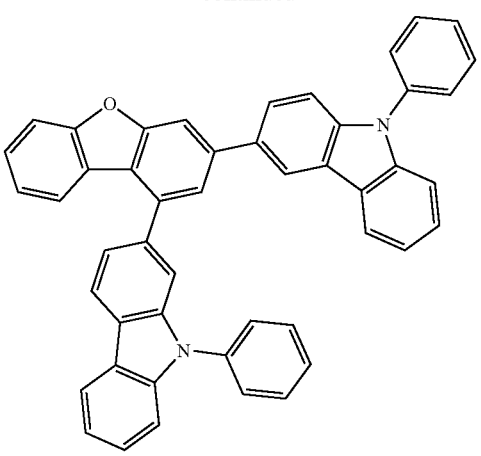
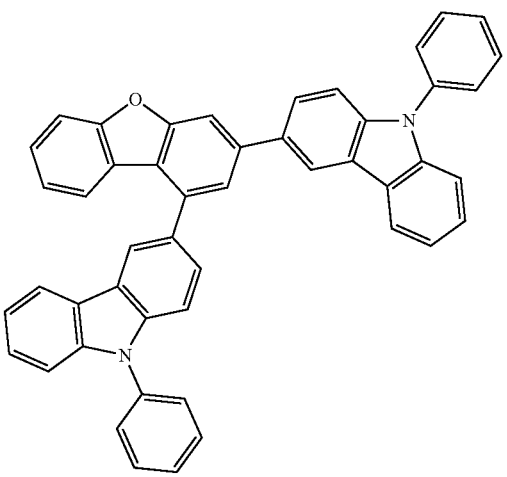
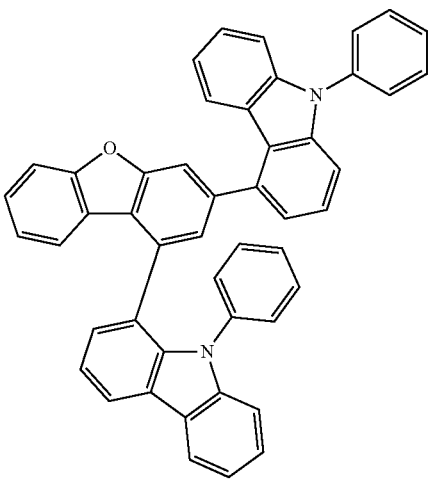

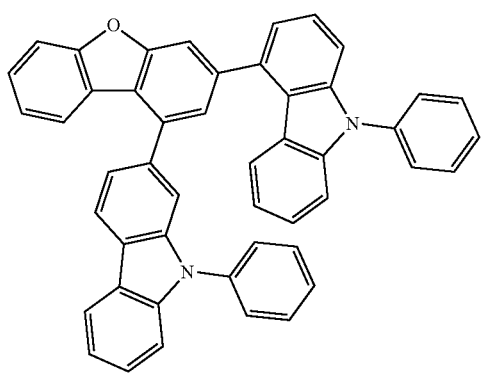
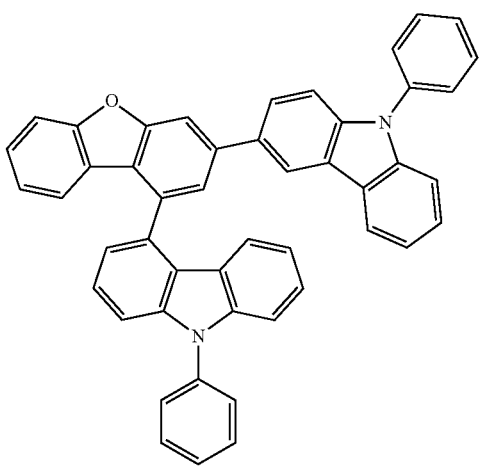
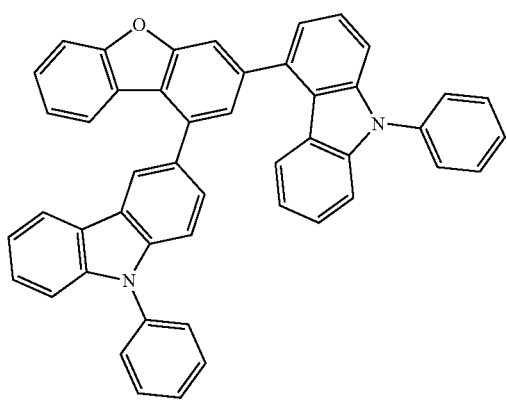
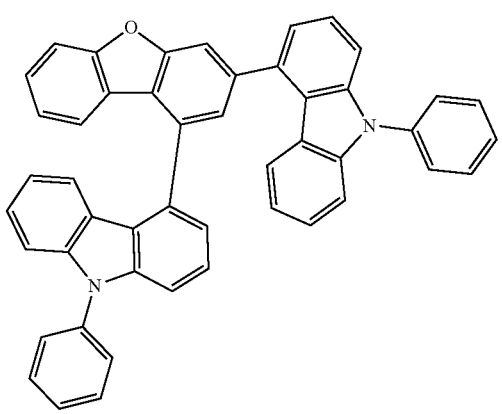
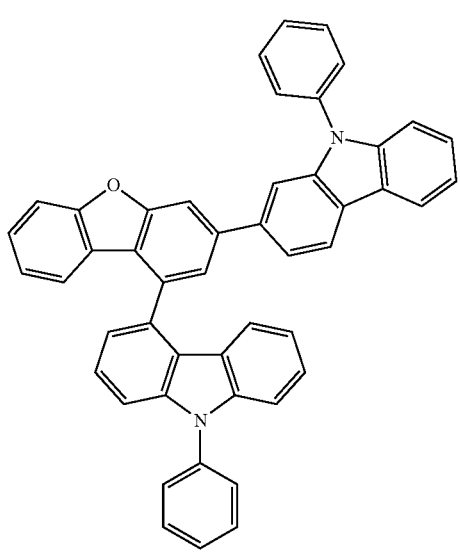
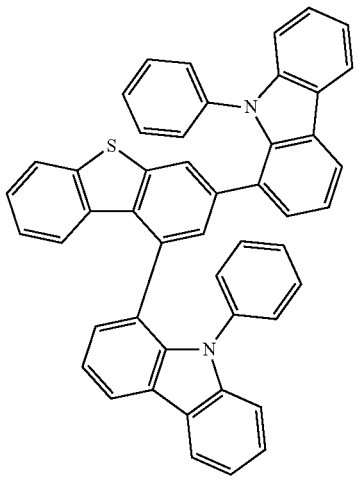

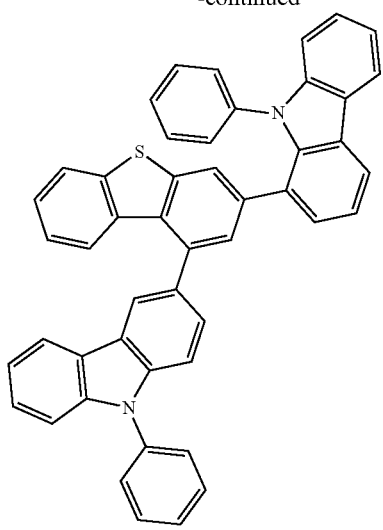
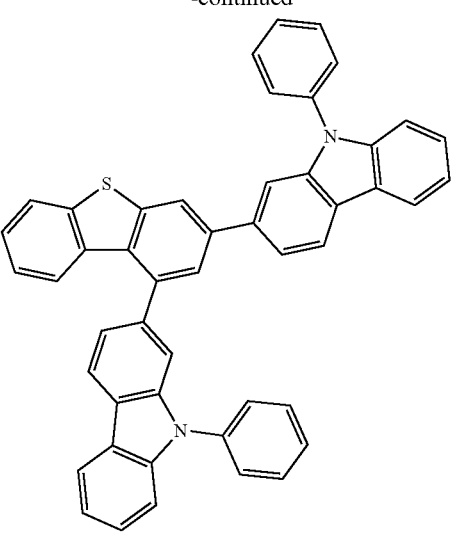
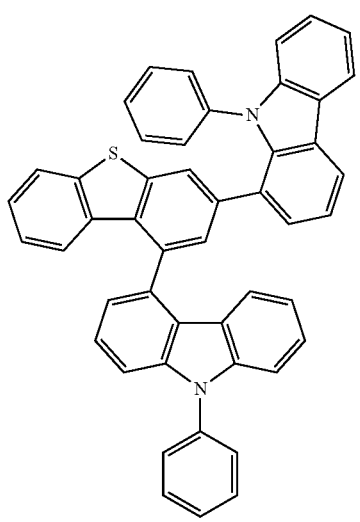
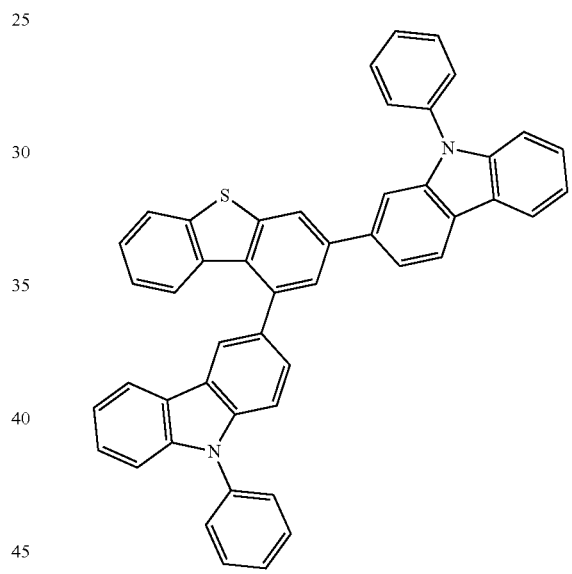
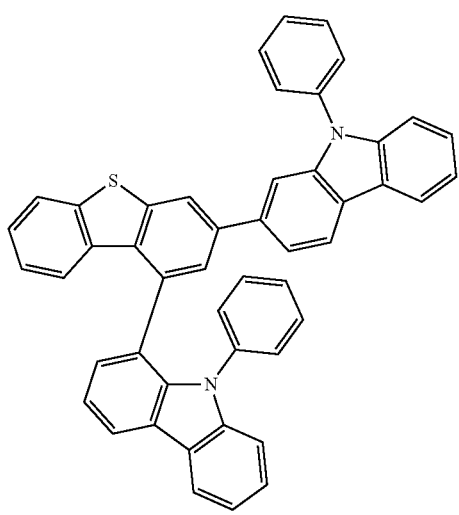
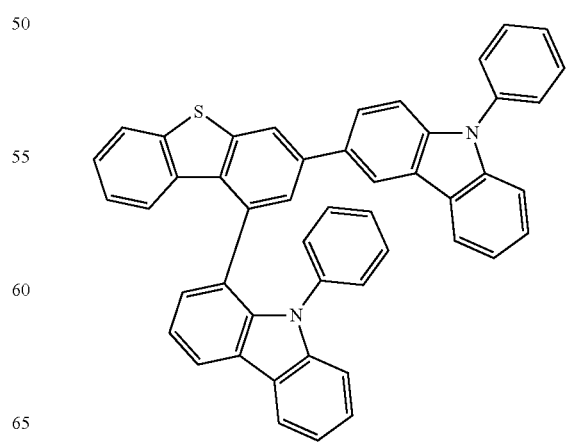

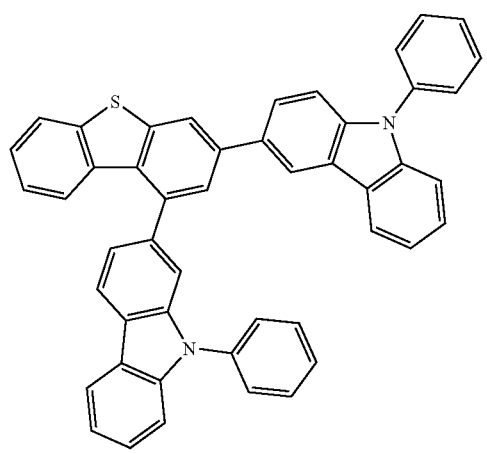
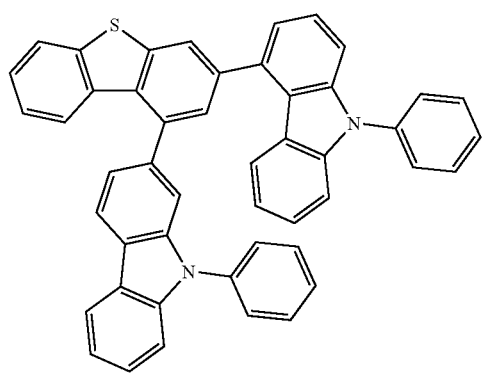
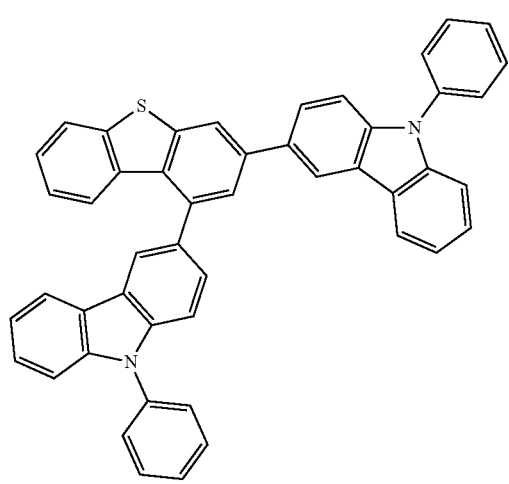
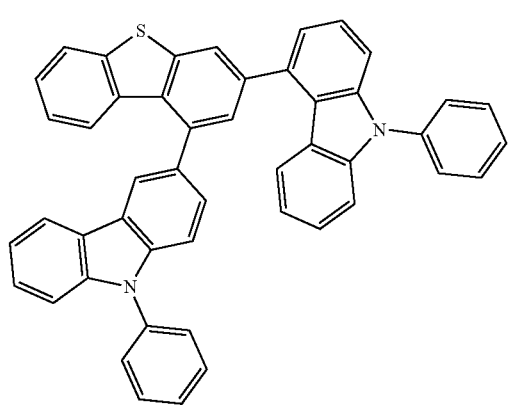
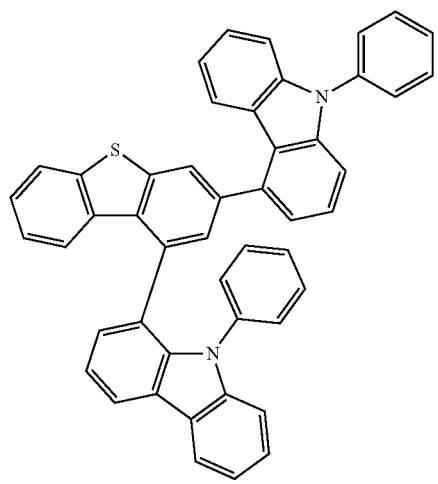
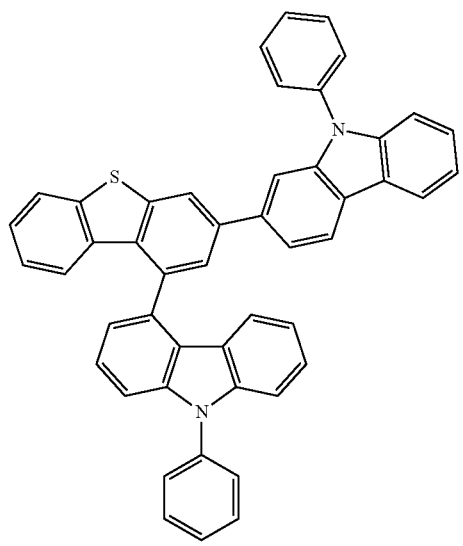

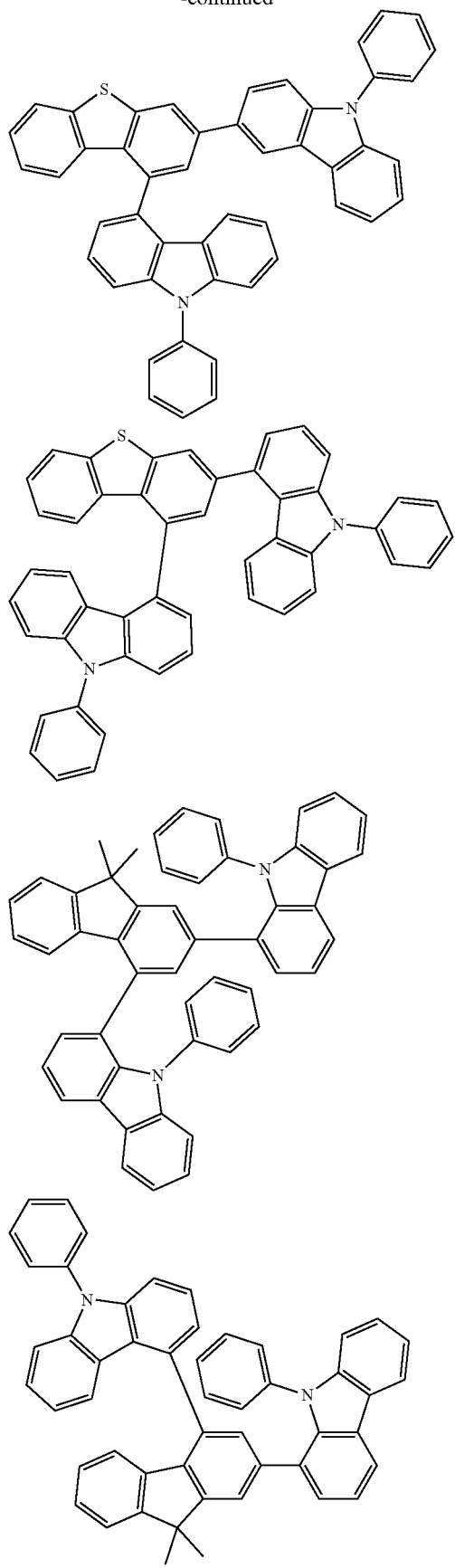
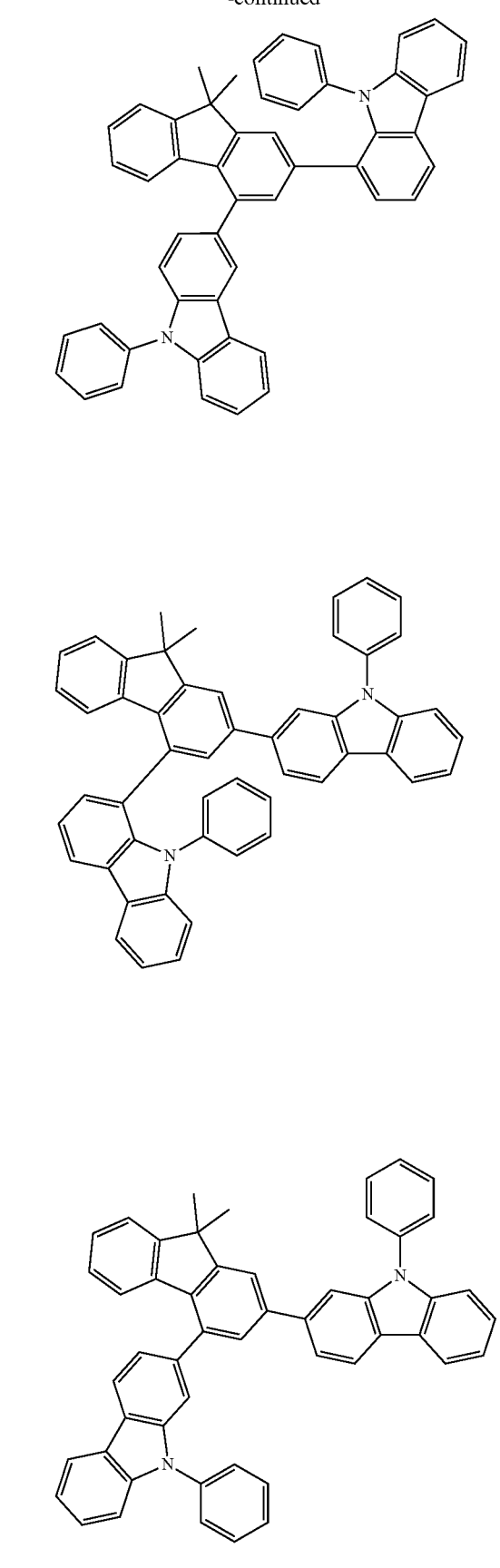

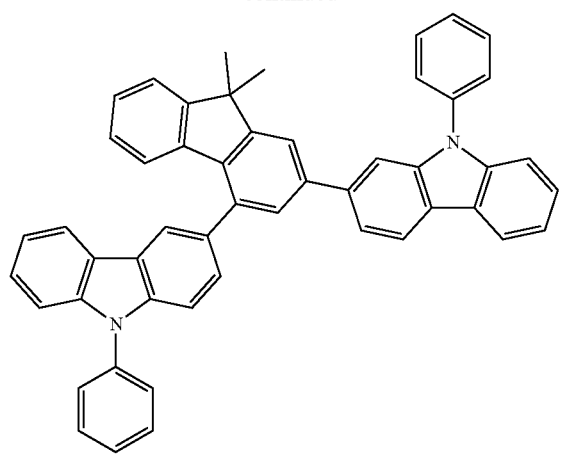
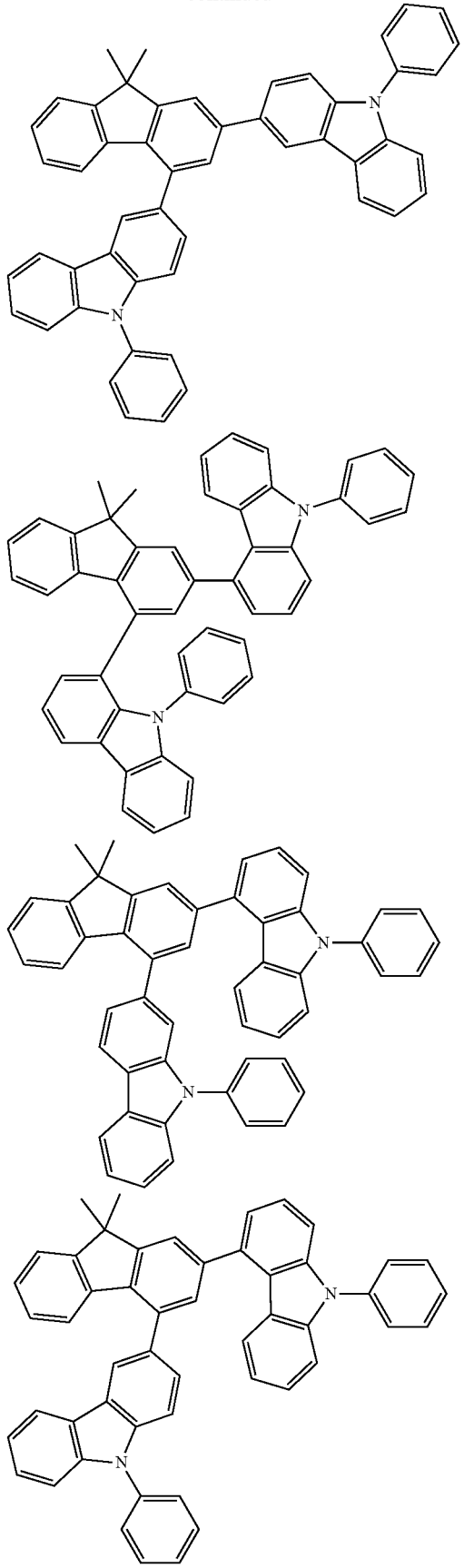

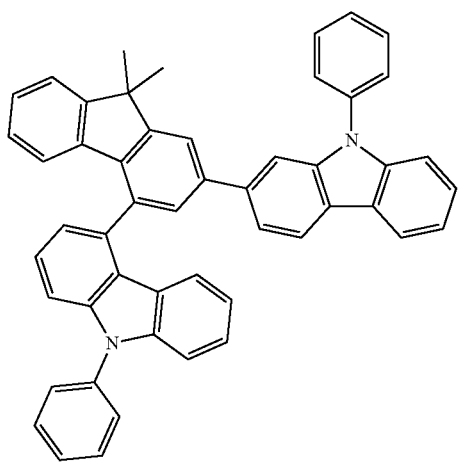
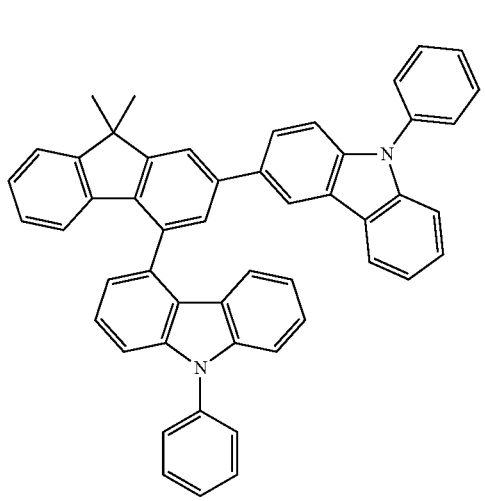
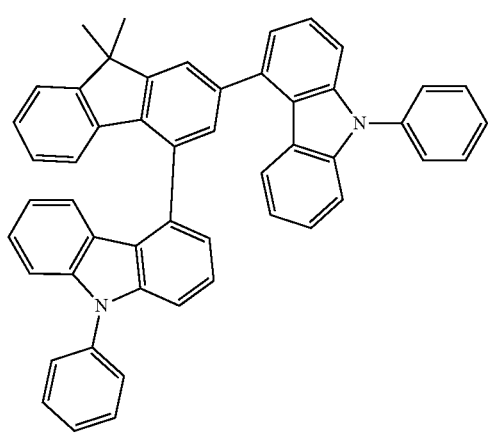
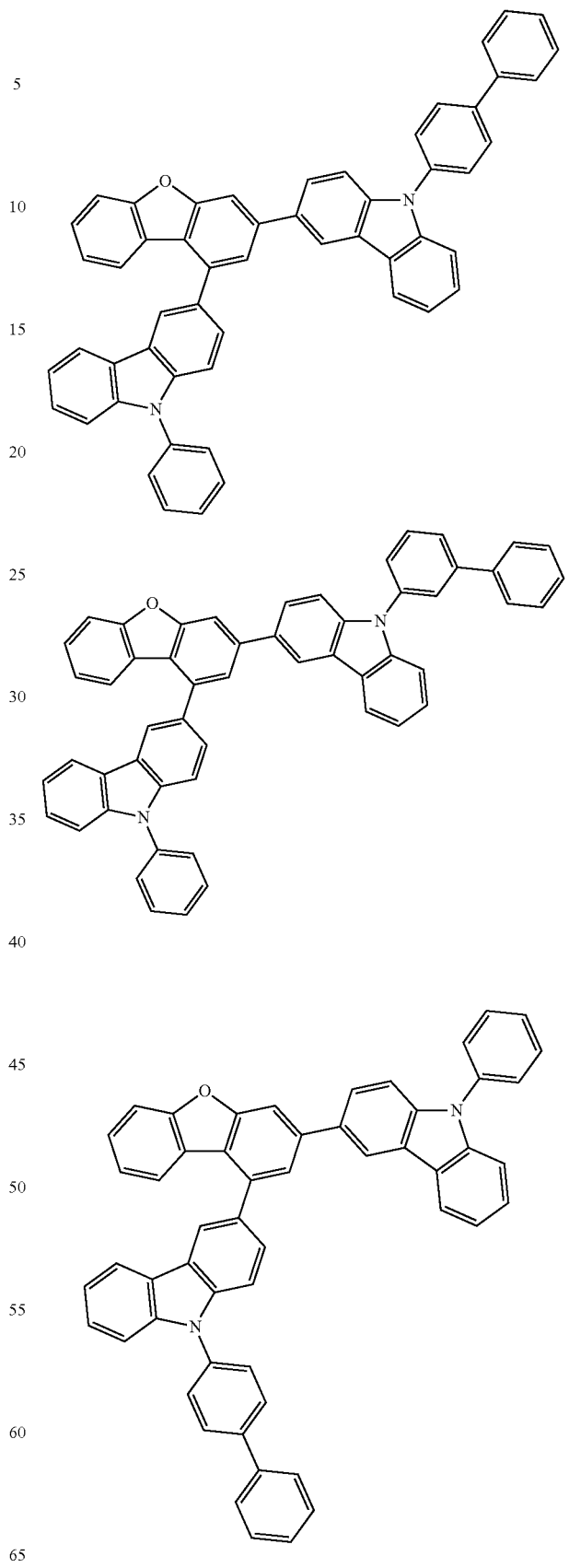

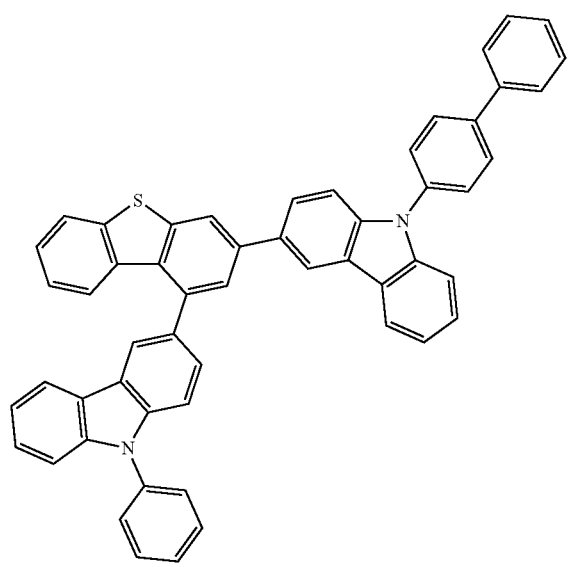
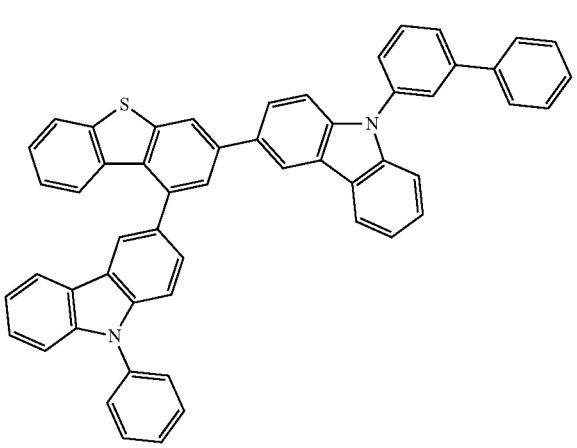
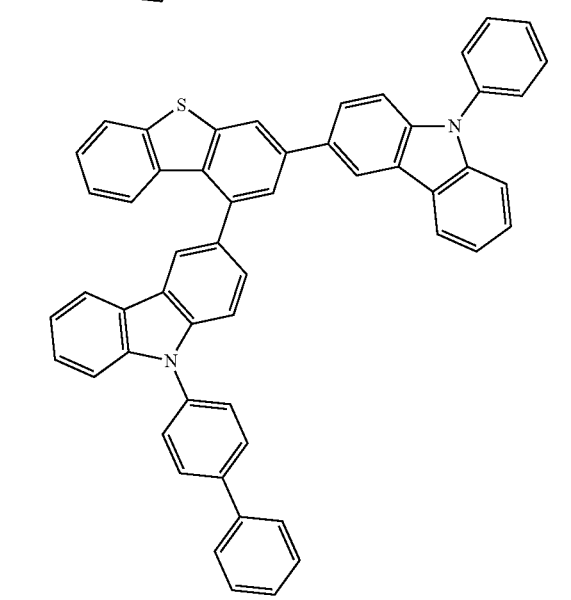
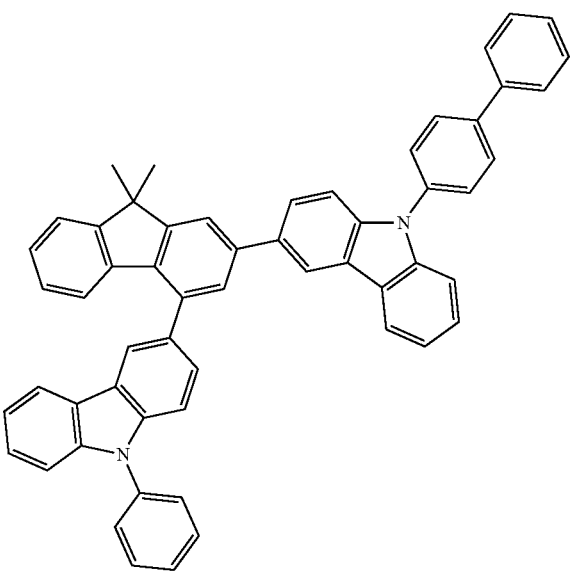
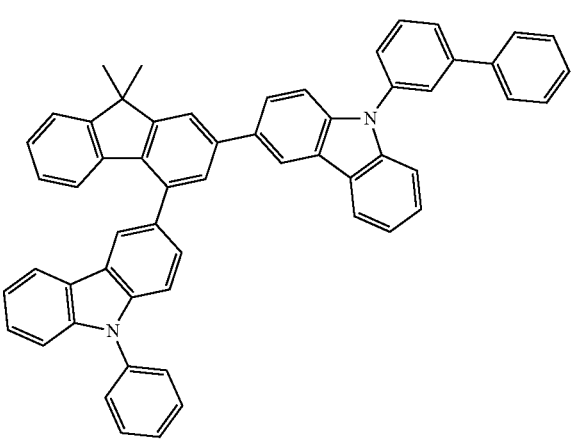

-continued

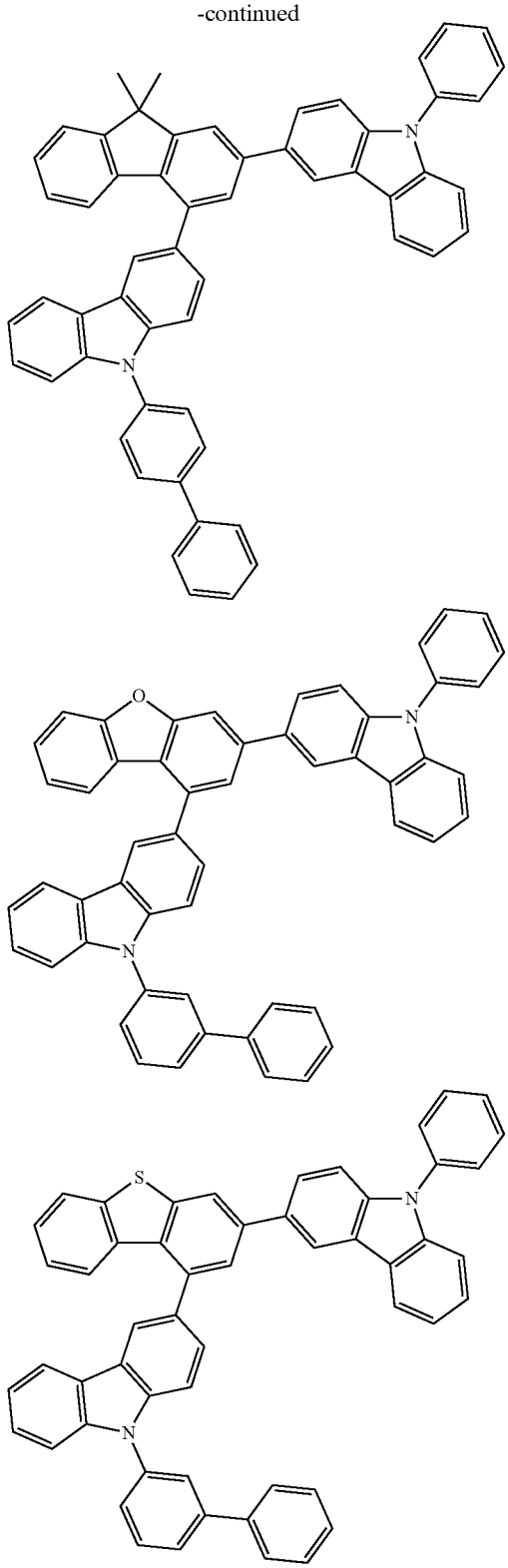

-continued

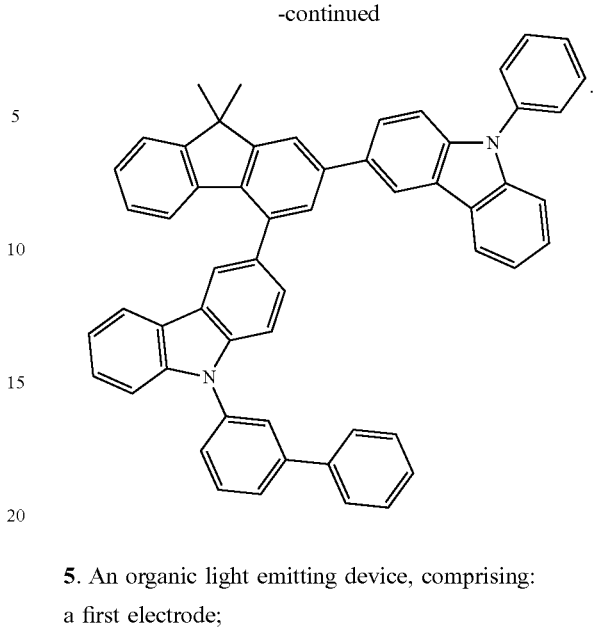

5. An organic light emitting device, comprising:
a first electrode;
a second electrode that is disposed opposite to the first electrode; and
one or more organic material layers that are disposed between the first electrode and the second electrode,
wherein one or more layers of the organic material layers include the compound of claim 1.

6. The organic light emitting device according to claim 5, wherein one of the one or more layers of the organic material layers that include-including the compound is a light emitting layer.

7. An organic light emitting device comprising a first electrode; a second electrode that is disposed opposite to the first electrode; and one or more organic material layers that are disposed between the first electrode and the second electrode, wherein one or more layers of the organic material layers include the compound of claim 2.

8. An organic light emitting device comprising a first electrode; a second electrode that is disposed opposite to the first electrode; and one or more organic material layers that are disposed between the first electrode and the second electrode, wherein one or more layers of the organic material layers include the compound of claim 3.

9. An organic light emitting device comprising a first electrode; a second electrode that is disposed opposite to the first electrode; and one or more organic material layers that are disposed between the first electrode and the second electrode, wherein one or more layers of the organic material layers include the compound of claim 4.

* * * * *